(12) United States Patent
Terada et al.

(10) Patent No.: US 7,781,425 B2
(45) Date of Patent: Aug. 24, 2010

(54) GUANIDINE COMPOUND AND ASYMMETRIC REACTION USING THE SAME

(75) Inventors: Masahiro Terada, Sendai (JP); Hitoshi Ube, Sendai (JP); Shigeko Yokoyama, Sendai (JP); Hideo Shimizu, Hiratsuka (JP)

(73) Assignee: Takasago International Coporation, Tokyo (JP)

( * ) Notice: Subject to any disclaimer, the term of this patent is extended or adjusted under 35 U.S.C. 154(b) by 973 days.

(21) Appl. No.: 10/589,814

(22) PCT Filed: Feb. 9, 2005

(86) PCT No.: PCT/JP2005/001943

§ 371 (c)(1),
(2), (4) Date: Sep. 21, 2006

(87) PCT Pub. No.: WO2005/077908

PCT Pub. Date: Aug. 25, 2005

(65) Prior Publication Data

US 2008/0154036 A1 Jun. 26, 2008

(30) Foreign Application Priority Data

Feb. 18, 2004 (JP) .............................. 2004-041181

(51) Int. Cl.
C07D 223/28 (2006.01)
C07D 301/00 (2006.01)
C07D 303/32 (2006.01)

(52) U.S. Cl. .................. 514/213.01; 514/217; 540/576; 540/587

(58) Field of Classification Search ............ 514/213.01, 514/217; 540/576, 587
See application file for complete search history.

(56) References Cited

U.S. PATENT DOCUMENTS 4,833,245 A 5/1989 Bruderer et al.
6,340,753 B1 1/2002 Maruoka

FOREIGN PATENT DOCUMENTS

| JP | 61-161266 | 7/1986 |
| JP | 2000-198774 | 7/2000 |
| JP | 2001-048866 | 2/2001 |

OTHER PUBLICATIONS

H. Y. Aboul-Enein et al., "Synthesis and Biological Activity of Dibenz[c,e]Azepines", Drug Design and Delivery, vol. 4, No. 1, pp. 27-33, 1989.
R. Chinchilla et al., "Enantiomerically Pure Guanidine-Catalysed Asymmetric Nitroaldol Reaction", Tetrahedron: Asymmetry, vol. 5, No. 7, pp. 1393-1402, 1994.
M. T. Allingham et al., "Synthesis and Applications of $C_2$-Symmetric Guanidine Bases", Tetrahedron Letters, vol. 44, No. 48, pp. 8677-8680, 2003.
T. Ooi et al., "Design of N-Spiro $C_2$-Symmetric Chiral Quaternary Ammonium Bromides as Novel Chiral Phase-Transfer Catalysts: Synthesis and Application to Practical Asymmetric Synthesis of α-Amino Acids", JACS Articles, No. 125, No. 17, pp. 5139-5151, 2003.
T. Ooi et al., "Practical Catalytic Enantioselective Synthesis of α,α-Dialkyl-α-Amino Acids by Chiral Phase-Transfer Catalysis", JACS, vol. 122, No. 21, pp. 5228-5229, 2000.
T. Ooi et al., "Molecular Design of a $C_2$-Symmetric Chiral Phase-Transfer Catalyst for Practical Asymmetric Synthesis of α-Amino Acids", JACS, vol. 121, No. 27, pp. 6519-6520, 1999.

*Primary Examiner*—Brenda L Coleman
(74) *Attorney, Agent, or Firm*—Wenderoth, Lind & Ponack, L.L.P.

(57) ABSTRACT

A guanidine compound having a biaryl skeleton represented by the following formula (1), which is useful as a catalyst for various asymmetric reactions.

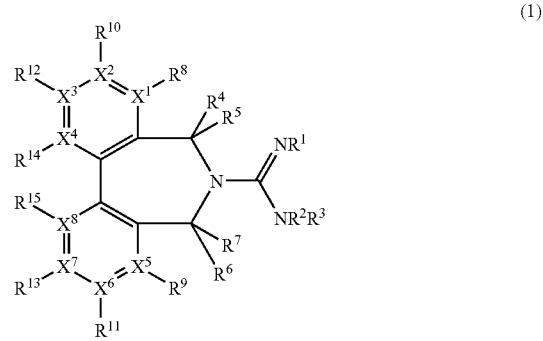

(1)

(wherein $R^1$, $R^2$ and $R^3$ each independently represent a hydrogen atom, a hydrocarbon group optionally having substituent(s), or a heterocyclic group optionally having substituent(s); $R^4$ to $R^{15}$ each independently represent a hydrogen atom, a hydrocarbon group optionally having substituent(s), a heterocyclic group optionally having substituent(s), a hydroxy group, an alkoxy group optionally having substituent(s), an aryloxy group optionally having substituent(s), an acyl group, an alkoxycarbonyl group optionally having substituent(s), an aryloxycarbonyl group optionally having substituent(s), a carbamoyl group optionally having substituent(s), an alkylthiocarbonyl group optionally having substituent(s), an arylthiocarbonyl group optionally having substituent(s), a carboxyl group, an alkylthio group optionally having substituent(s), an arylthio group optionally having substituent(s), an amino group or a substituted amino group, or a substituted silyl group; or in any combination of $R^1$ to $R^{15}$, these substituents may be taken together to form a ring; and $X^1$ to $X^8$ represent a hydrogen atom or a nitrogen atom, provided that, in the case of a nitrogen atom, there is no substituent on $X^1$ to $X^8$.

3 Claims, No Drawings

GUANIDINE COMPOUND AND ASYMMETRIC REACTION USING THE SAME

This application is a U.S. national stage of International Application No. PCT/JP2005/001943 filed Feb. 9, 2005.

TECHNICAL FIELD

The present invention relates to a guanidine compound and an asymmetric reaction using said compound.

BACKGROUND ART

In recent years, attention has been paid to optically active guanidine compounds as base catalysts for asymmetric nucleophilic-type reactions, a representative of which is an asymmetric aldol-type reaction. However, all of the previously known optically active guanidine compounds have central chirality as a chiral element, and it cannot be said that molecular design based on only such the central chirality is sufficient to draw the potential usefulness of such optically active guanidine compounds. As one of the reactions using an optically active guanidine compound which is constructed based on central chirality as an asymmetric base catalyst, a nitroaldol reaction is reported (Non-Patent Literature 1: Tetrahedron: Asymmetry, 1994, 5, 1393; Non-Patent Literature 2: Tetrahedron Lett., 2003, 44, 8677). The Non-Patent Literature 1 disclosed that in the aldol condensation between benzaldehyde and nitromethane, optically active guanidines having a phenethylamine skeleton as an optically active site are used as an asymmetric catalyst, and 2-nitro-1-phenylethanol is obtained in a yield of 31% and an asymmetric yield of 33% ee.

DISCLOSURE OF THE INVENTION

Problems to be Solved by the Invention

However, there are few reports on asymmetric aldol-type reactions using an optically active guanidine as an asymmetric catalyst and, in the aforementioned literatures, both of yield and asymmetric yield are not satisfactory.

Means to Solve the Problems

The present inventors have continued to intensively study and, as a result, created guanidine compounds having a biaryl skeleton, particularly novel optically active guanidine compounds based on axial chirality, and have found that these guanidine compounds act as an effective catalyst in asymmetric nucleophilic addition reaction such as asymmetric aldol-type reaction, asymmetric Michael addition reaction, and asymmetric epoxidation reaction. The present invention has been completed based on these findings. That is, the present invention relates to:

1. a guanidine compound having a biaryl skeleton represented by the formula (1).

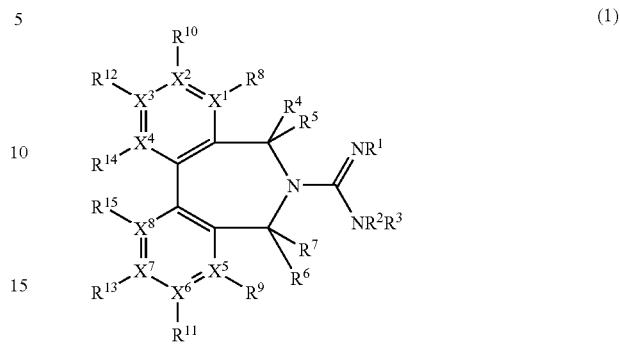

(wherein $R^1$, $R^2$ and $R^3$ each independently represent a hydrogen atom, a hydrocarbon group optionally having substituent(s), or a heterocyclic group optionally having substituent(s); $R^4$ to $R^{15}$ each independently represent a hydrogen atom, a hydrocarbon group optionally having substituent(s), a heterocyclic group optionally having substituent(s), a hydroxy group, an alkoxy group optionally having substituent(s), an aryloxy group optionally having substituent(s), an acyl group, an alkoxycarbonyl group optionally having substituent(s), an aryloxycarbonyl group optionally having substituent(s), a carbamoyl group optionally having substituent(s), an alkylthiocarbonyl group optionally having substituent(s), an arylthiocarbonyl group optionally having substituent(s), a carboxyl group, an alkylthio group optionally having substituent(s), an arylthio group optionally having substituent(s), an amino group or a substituted amino group, a substituted silyl group or a halogen atom, and in any combination of $R^1$ to $R^{15}$, these substituents may be taken together to form a ring; and $X^1$ to $X^8$ represent a carbon atom or a nitrogen atom, provided that when $X^1$ to $X^8$ represent a nitrogen atom, there is no substituent on $X^1$ to $X^8$);

2. the guanidine compound according to the above 1, which is optically active;

3. the optically active guanidine compound according to the above 2, which is an optically active substance based on axial chirality;

4. an asymmetric nucleophilic addition reaction, which is performed in the presence of the optically active guanidine compound as defined in the above 2 or 3;

5. the asymmetric nucleophilic addition reaction according to the above 4, which comprises reacting a carbonyl compound or an imine compound with a compound having at least one hydrogen atom on the carbon atom adjacent to an electron-withdrawing group or a nucleophilic agent in the presence of the guanidine compound as defined in 2 or 3;

6. The asymmetric nucleophilic addition reaction according to the above 5, wherein the carbonyl compound or the imine compound is represented by the following formula (2):

wherein $R^{16}$ and $R^{17}$ each independently represent a hydrogen atom, a hydrocarbon group optionally having substituent(s) or a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s) or a carbamoyl group optionally having substituent(s), and Y represents an oxygen atom or $NR^{18}$, wherein $R^{18}$ represents a hydrogen atom, a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), a carbamoyl group optionally having substituent(s) or an amino group optionally having substituent(s);

7. the asymmetric nucleophilic addition reaction according to 5 or 6, wherein the compound having at least one hydrogen atom on the carbon atom adjacent to an electron-withdrawing group is a compound represented by the following formula (3):

$$R^{19}R^{20}CHQ^1 \qquad (3)$$

(wherein $R^{19}$ and $R^{20}$ each independently represent a hydrogen atom, a hydrocarbon group optionally having substituent(s), a heterocyclic group optionally having substituent(s), an alkoxy group optionally having substituent(s), a hydroxy group, an amino group, a substituted amino group, an alkylthio group optionally having substituent(s), an arylthio group optionally having substituent(s), an acyl group, an alkoxycarbonyl group optionally having substituent(s), an alkylthiocarbonyl group optionally having substituent(s), an aryloxycarbonyl group optionally having substituent(s), an arylthiocarbonyl group optionally having substituent(s), a carbamoyl group optionally having substituent(s), a substituted imino group, a cyano group, a nitro group or a halogen atom; and $Q^1$ represents an electron-withdrawing group;

8. the asymmetric nucleophilic addition reaction according to any one of the above 5 to 7, wherein the nucleophilic agent is a cyanide or a phosphonate or a hydroxy-di-substituted phosphine ($HP(=O)(R^{21})_2$ or $HOP(R^{21})_2$), wherein $R^{21}$ represents a hydrocarbon group optionally having substituent(s), a heterocyclic group optionally having substituent(s), an alkoxy group optionally having substituent(s) or an aryloxy group optionally having substituent(s));

9. the asymmetric nucleophilic addition reaction according to any one of the above 5 to 8, wherein in the compound of the formula (3), $Q^1$ is a nitro group, a cyano group, $C(=O)R^{22}$ ($R^{22}$ represents a hydrocarbon group optionally having substituent(s), a heterocyclic group optionally having substituent(s), an alkoxy group optionally having substituent(s), an aryloxy group optionally having substituent(s), an alkylthio group optionally having substituent(s), an arylthio group optionally having substituent(s) or an amino group optionally having substituent(s)), or an acyl group derived from a sulfonic acid or a phosphonic acid;

10. an asymmetric Michael addition reaction, wherein the asymmetric nucleophilic addition reaction as defined in the above 4 is performed with an $\alpha,\beta$-unsaturated compound, and a compound having at least one hydrogen atom on the carbon atom adjacent to an electron-withdrawing group or a nucleophilic agent;

11. the asymmetric Michael addition reaction according to the above 10, wherein the $\alpha,\beta$-unsaturated compound is a compound represented by the following formula (4):

$$R^{23}R^{24}C=CR^{25}Q^2 \qquad (4)$$

(wherein $R^{23}$ to $R^{25}$ each independently represent a hydrogen atom, a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), a carbamoyl group optionally having substituent(s), a cyano group, a nitro group, a halogen atom, an alkoxy group optionally having substituent(s), an aryloxy group optionally having substituent(s), an alkylthio group optionally having substituent(s) or an arylthio group optionally having substituent(s); and $Q^2$ represents an electron-withdrawing group, or in any combination of $R^{23}$ to $R^{25}$ and $Q^2$, these substituents may be taken together to form a ring);

12. the asymmetric Michael addition reaction according to the above 10 or 11, wherein the compound having at least one hydrogen atom on the carbon atom adjacent to an electron-withdrawing group is a compound represented by the formula (3);

13. the asymmetric Michael addition reaction according to the above 11 or 12, wherein the nucleophilic agent is a compound represented by the following formula (6):

$$R^{26}ZH \qquad (6)$$

(wherein Z represents an oxygen atom, a sulfur atom or a nitrogen atom optionally having substituent(s); when Z represents an oxygen atom or a sulfur atom, $R^{26}$ represents a hydrogen atom, a hydrocarbon group optionally having substituent(s), a heterocyclic group optionally having substituent(s), an amino group optionally having substituent(s), an acyl group or a cyano group; when Z represents a nitrogen atom optionally having substituent(s), $R^{26}$ represents a hydrogen atom, a hydrocarbon group optionally having substituent(s), a heterocyclic group optionally having substituent(s), an alkoxy group optionally having substituent(s), an aryloxy group optionally having substituent(s), an amino group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), or a carbamoyl group optionally having substituent(s)), a cyanide, an azide, a phosphonate or a hydroxyl-di-substituted phosphine ($HP(=O)(R^{21})_2$ or $HOP(R^{21})_2$), wherein $R^{21}$ represents a hydrocarbon group optionally having substituent(s), a heterocyclic group optionally having substituent(s), an alkoxy group optionally having substituent(s) or an aryloxy group optionally having substituent(s));

14. an asymmetric epoxidation reaction, which is performed in the presence of the guanidine compound as defined in the above 2 or 3;

15. the asymmetric epoxidation reaction according to the above 14, wherein an $\alpha,\beta$-unsaturated compound and a peroxy compound are reacted;

16. the asymmetric epoxidation reaction according to the above 15, wherein the $\alpha,\beta$-unsaturated compound is a compound represented by the formula (4);

17. the asymmetric epoxidation reaction according to the above 15 or 16, wherein the peroxy compound is a compound represented by the following formula (7):

$$R^{26}OOH \qquad (7)$$

wherein $R^{26}$ represents a hydrogen atom, a hydrocarbon group optionally having substituent(s), a heterocyclic group optionally having substituent(s) or an acyl group;

18. a process for producing an optically active compound represented by the following formula (9a) or (9b):

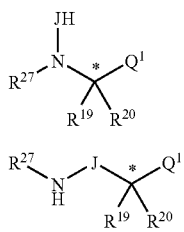

(wherein $R^{27}$ represents a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), or a carbamoyl group optionally having substituent(s), and J represents an oxygen atom or $NR^{28}$ ($R^{28}$ represents a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), or a carbamoyl group optionally having substituent(s)); $R^{19}$, $R^{20}$, and $Q^1$ are the same as defined above; and * represents an asymmetric carbon atom), which comprises reacting a nitrogen-containing compound represented by the following formula (8):

$$R^{27}N=J \tag{8}$$

(wherein $R^{27}$ and J are the same as defined above), and a compound represented by the following formula (3):

$$R^{19}R^{20}CHQ^1 \tag{3}$$

(wherein $R^{19}$, $R^{20}$ and $Q^1$ are the same as defined above) in the presence of the guanidine compound as defined in the above 2 or 3;

19. a process for producing an optically active compound by dissymmetric procedure, which comprises the Wittig-reaction between a carbonyl compound having a skeleton which has σ symmetry and produces an asymmetric carbon after the reaction, and a phosphorus compound represented by the following formula (10):

$$R^{28}R^{29}CHP(=O)R^{30}R^{31} \tag{10}$$

(wherein $R^{28}$ and $R^{29}$ each independently represent a hydrogen atom, a hydrocarbon group optionally having substituent(s), a heterocyclic group optionally having substituent(s), an alkoxy group optionally having substituent(s), a hydroxy group, a substituted amino group, an alkylthio group optionally having substituent(s), an acyl group, an alkoxycarbonyl group optionally having substituent(s), an alkylthiocarbonyl group optionally having substituent(s), a carbamoyl group optionally having substituent(s), a substituted imino group, a cyano group, a nitro group or a halogen atom, provided that $R^{28}$ and $R^{29}$ are not the same substituent, and $R^{30}$ and $R^{31}$ each independently represent a hydrocarbon group optionally having substituent(s), a heterocyclic group optionally having substituent(s), an alkoxy group optionally having substituent(s) or an aryloxy group optionally having substituent(s)) in the presence of the guanidine compound as defined in the above 2 or 3.

Effect of the Invention

According to the present invention, asymmetric addition reaction such as asymmetric aldol-type reaction, asymmetric Michael addition reaction, and asymmetric epoxidation reaction proceeds effectively.

THE BEST MODE FOR CARRYING OUT THE INVENTION

The present invention will be explained in detail below.

In the compounds represented by the formula (1) of the present invention, examples of the hydrocarbon group in a hydrocarbon group optionally having substituent(s) include an alkyl group which may be straight-chain, branched, or cyclic. The alkyl group is preferably, for example, a straight-chain or branched or cyclic alkyl group of 1 to 20 carbon atom(s), preferably 1 to 10 carbon atom(s), more preferably 1 to 6 carbon atom(s), and specifically includes straight-chain or branched alkyl groups such as methyl, ethyl, n-propyl, isopropyl, n-butyl, sec-butyl, isobutyl, tert-butyl, n-pentyl, neopentyl, tert-pentyl, hexyl, heptyl, octyl, nonyl, decyl, cetyl, and stearyl, and the like; and cycloalkyl groups such as cyclopentyl, methylcyclopentyl, cyclohexyl, methylcyclohexyl, and cyclooctyl, and the like.

Further, these alkyl groups may have substituent(s), and examples of such substituent include a hydrocarbon group, an aliphatic heterocyclic group, an aromatic heterocyclic group, an alkoxy group, an alkylenedioxy group, an aryloxy group, an aralkyloxy group, a heteroaryloxy group, an alkylthio group, an arylthio group, an aralkylthio group, a heteroarylthio group, an amino group, a substituted amino group, a cyano group, a hydroxy group, an oxo group, a nitro group, a mercapto group, a tri-substituted silyl group and a halogen atom, and the like.

Examples of the hydrocarbon group as a substituent for the alkyl group include an alkyl group, an alkenyl group, an alkynyl group, an aryl group, an aralkyl group, and the like.

The alkyl group is preferably, for example, a straight-chain or branched or cyclic alkyl group of 1 to 20 carbon atom(s), and examples of the alkyl group include straight or branched alkyl groups such as methyl, ethyl, n-propyl, isopropyl, n-butyl, sec-butyl, isobutyl, tert-butyl, n-pentyl, neopentyl, tert-pentyl, hexyl, heptyl, octyl, nonyl, decyl, cetyl, stearyl, and the like; and cycloalkyl groups such as cyclopentyl, cyclohexyl, cyclooctyl, and the like.

The alkenyl group is, for example, a straight-chain or branched alkenyl group of 2 to 15 carbon atoms, preferably 2 to 10 carbon atoms, more preferably of 2 to 6 carbon atoms, and examples of such alkenyl group include ethenyl, propenyl, 1-butenyl, pentenyl, hexenyl, and the like.

The alkynyl group is, for example, a straight-chain or branched alkynyl group of 2 to 15 carbon atoms, preferably 2 to 10 carbon atoms, more preferably 2 to 6 carbon atoms, and examples of such alkynyl group include ethynyl, 1-propynyl, 2-propynyl, 1-butynyl, 3-butynyl, pentynyl, hexynyl, and the like.

The aryl group is, for example, an aryl group of 6 to 20 carbon atoms, and examples of such aryl group include phenyl, naphthyl, anthryl, phenanthryl, biphenyl, terphenyl, and the like.

The aralkyl group is, for example, a group in which at least one hydrogen atom of the alkyl group is substituted with the aforementioned aryl group, and is preferably an aralkyl group of 7 to 12 carbon atoms, and examples of such aralkyl group include benzyl, 2-phenylethyl, 1-phenylpropyl, 3-naphthylpropyl, and the like.

The aliphatic heterocyclic group is, for example, a 5- to 8-membered, preferably 5- or 6-membered monocyclic aliphatic heterocyclic group, or polycyclic or fused aliphatic heterocyclic group, having 2 to 14 carbon atoms and containing at least one heteroatom, preferably 1 to 3 heteroatom(s) such as a nitrogen atom, an oxygen atom, a sulfur atom, and the like as a heteroatom. Examples of the aliphatic heterocyclic group include pyrrolidyl-2-one, piperidino, piperazinyl, morpholino, tetrahydrofuryl, tetrahydropyranyl, tetrahydrothienyl, and the like.

The aromatic heterocyclic group is, for example, a 5- to 8-membered, preferably 5- or 6-membered monocyclic heteroaryl group, or polycyclic or fused heteroaryl group, having 2 to 15 carbon atoms and containing at least one heteroatom, preferably 1 to 3 heteroatom(s) such as a nitrogen atom, an oxygen atom, a sulfur atom, and the like as a heteroatom, and examples of the aromatic heterocyclic group include furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzimidazolyl, benzooxazolyl, benzothiazolyl, and the like.

The alkoxy group is, for example, an alkoxy group of 1 to 6 carbon atom(s), which may be straight-chain, branched or cyclic, and examples of such alkoxy group include methoxy, ethoxy, n-propoxy, isopropoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, cyclohexyloxy, methoxymethoxy, 2-ethoxyethoxy, and the like.

The alkylenedioxy group is, for example, an alkylenedioxy group of 1 to 3 carbon atom(s), and examples of such alkylenedioxy group include methylenedioxy, ethylenedioxy, trimethylenedioxy, propylenedioxy, isopropylidenedioxy, and the like.

The aryloxy group is, for example, an aryloxy group of 6 to 14 carbon atoms, and examples of such aryloxy group include phenoxy, tolyloxy, xylyloxy, naphthoxy, anthryloxy, and the like.

The aralkyloxy group is, for example, an aralkyloxy group of 7 to 12 carbon atoms, and examples of such aralkyloxy group include benzyloxy, 4-methoxyphenylmethoxy, 1-phenylethoxy, 2-phenylethoxy, 1-phenylpropoxy, 2-phenylpropoxy, 3-phenylpropoxy, 1-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy, and the like.

The heteroaryloxy group is, for example, a heteroaryloxy group of 2 to 14 carbon atoms, containing at least one heteroatom, preferably 1 to 3 heteroatom(s) such as a nitrogen atom, an oxygen atom, a sulfur atom, and the like as a heteroatom, and examples of such heteroaryloxy group include 2-pyridyloxy, 2-pyrazyloxy, 2-pyrimidyloxy, 2-quinolyloxy, and the like.

The alkylthio group is, for example, an alkylthio group of 1 to 6 carbon atom(s), which may be straight-chain, branched or cyclic, and examples of such alkylthio group include methylthio, ethylthio, n-propylthio, isopropylthio, n-butylthio, 2-butylthio, isobutylthio, tert-butylthio, pentylthio, hexylthio, cyclohexylthio, and the like.

The arylthio group is, for example, an arylthio group of 6 to 14 carbon atoms, and examples of such arylthio group include phenylthio, tolylthio, xylylthio, naphthylthio, and the like.

The aralkylthio group is an aralkylthio group of 7 to 12 carbon atoms, and examples of such aralkylthio group include benzylthio, 2-phenethylthio, and the like.

The heteroarylthio group is, for example, a heteroarylthio group of 2 to 14 carbon atoms, containing at least one heteroatom, preferably 1 to 3 heteroatom(s) such as a nitrogen atom, an oxygen atom, a sulfur atom, and the like as a heteroatom, and examples of such heteroarylthio group include 4-pyridylthio, 2-benzimidazolylthio, 2-benzoxazolylthio, 2-benzothiazolylthio, and the like.

Examples of the substituted amino group include an amino group wherein 1 or 2 hydrogen atom(s) of the amino group is/are substituted with a substituent such as an alkyl group, an aryl group, or an aralkyl group, or the like.

The amino group substituted with an alkyl group, i.e. an alkyl-substituted amino group includes a mono- or di-alkylamino group such as N-methylamino, N,N-dimethylamino, N,N-diethylamino, N,N-diisopropylamino, N-cyclohexylamino, and the like.

The amino group substituted with an aryl group, i.e. an aryl-substituted amino group includes a mono- or di-aryl amino group such as N-phenylamino, N,N-diphenylamino, N,N-ditolylamino, N-naphthylamino, N-naphthyl-N-phenylamino, and the like.

Examples of the amino group substituted with an aralkyl group, i.e. an aralkyl-substituted amino group includes a mono- or di-aralkylamino group such as N-benzylamino, N,N-dibenzylamino, and the like.

Examples of the tri-substituted silyl group include trimethylsilyl, triethylsilyl, triisopropylsilyl, tert-butyldimethylsilyl, tert-butyldiphenylsilyl, triphenylsilyl, and the like.

Examples of the halogen atom include a fluorine atom, a chlorine atom, a bromine atom, and an iodine atom, and examples of the halogenated alkyl group include monofluoromethyl, difluoromethyl, trifluoromethyl, pentafluoroethyl, and the like.

Among these substituents, the hydrocarbon group, the aliphatic heterocyclic group, the aromatic heterocyclic group, the alkoxy group, the alkylenedioxy group, the aryloxy group, the aralkyloxy group, the heteroaryloxy group, the alkylthio group, the arylthio group, the aralkylthio group, the heteroarylthio group or the substituted amino group may be further substituted with a group selected from the group consisting of the aforementioned substituents.

In addition, one embodiment of the hydrocarbon group in the compound of the formula (1) is, for example, an alkenyl group which may be straight-chain or cyclic or branched, and examples of such alkenyl group include vinyl, 1-propenyl, 2-propenyl, 1-butenyl, 2-butenyl, 3-butenyl, 1-pentenyl, 2-pentenyl, 3-pentenyl, 4-pentenyl, 1-cyclopentenyl, 3-cyclopentenyl, 1-hexenyl, 2-hexenyl, 3-hexenyl, 4-hexenyl, 5-hexenyl, 1-cyclohexenyl, 3-cyclohexenyl group, and the like.

Further, these alkenyl groups may have a substituent, and the substituent is, for example, an alkyl group, a halogen atom, an aryl group, and a heterocyclic group, and the like, specifically including those described above.

In addition, one embodiment of the hydrocarbon group in the compound of the formula (1) is, for example, an alkynyl group which may be straight-chain or branched, and examples of such alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like.

In addition, these alkynyl groups may have a substituent, such as an alkyl group, an aryl group, a heterocyclic group, a tri-substituted silyl group, and the like, and specific examples of the alkyl group, the aryl group, and the heterocyclic group include those as described above.

In addition, one embodiment of the hydrocarbon group in the compound of the formula (1) is an aryl group, and examples of such aryl group include the aforementioned aryl groups. Further, these aryl groups may have a substituent such as an alkyl group, an aryl group, a heterocyclic group, a halogen atom, and the like, and specific examples include those described above.

The heterocyclic group in the compound of the formula (1) is, for example, an aliphatic or aromatic heterocyclic group, and examples of such heterocyclic group include the aforementioned heterocyclic groups. These heterocyclic groups may have a substituent such as an alkyl group, an aryl group, a heterocyclic group, and the like, and specific examples include those described above.

Examples of the alkoxy group optionally having substituent(s) include an alkoxy group and a substituted alkoxy group. The alkoxy group is, for example, an alkoxy group of 1 to 20 carbon atom(s), which may be straight-chain, branched or cyclic, and specific examples of such alkoxy group include methoxy, ethoxy, n-propoxy, isopropoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, heptyloxy, octyloxy, nonyloxy, decyloxy, cyclohexyloxy, methoxymethoxy, benzyloxy, and the like. Inter alia, the alkoxy group is preferably an alkoxy group of 1 to 10 carbon atom(s).

Examples of the aryloxy group optionally having substituent(s) include an aryloxy group and a substituted aryloxy group. The aryloxy group is, for example, an aryloxy group of 6 to 20 carbon atoms, and examples of such aryloxy group include phenoxy, naphthoxy, anthryloxy, and the like. Examples of the substituent include the aforementioned alkyl group, alkoxy group, halogen atom, aryl group, and the like. Inter alia, the aryloxy group is preferably an aryloxy group of 6 to 14 carbon atoms.

Examples of the acyl group include a straight-chain, branched or cyclic acyl group of 1 to 20 carbon atom(s) derived from carboxylic acids, sulfonic acids, sulphinic acids, phosphinic acids, phosphonic acids, and the like.

The carboxylic acid-derived acyl group is, for example, an acyl group derived from carboxylic acids such as aliphatic carboxylic acids, aromatic carboxylic acids, and the like, and specific examples of the carboxylic acid-derived acyl group include formyl, acetyl, propionyl, butyryl, pivaloyl, pentanoyl, hexanoyl, lauroyl, stearoyl, benzoyl, 1-naphthoyl, 2-naphthoyl, trifluoroacetyl, and the like. Inter alia, the acyl group is preferably an acyl group of 2 to 18 carbon atoms.

Examples of the sulfonic acid-derived acyl group include an alkylsulfonyl group such as methanesulfonyl and the like, a halogenated alkyl sulfonyl group such as trifluoromethanesulfonyl and the like, an arylsulfonyl group such as benzenesulfonyl, p-toluenesulfonyl, and the like.

Examples of the sulfinic acid-derived acyl group include an alkylsulfinyl group such as methanesulfinyl and the like, an arylsulfinyl group such as benzenesulfinyl and the like.

Examples of the phosphinic acid-derived acyl group include a dialkylphosphinyl group such as dimethylphosphinyl and the like, and a diarylphosphinyl group such as diphenylphosphinyl and the like.

Examples of the phosphonic acid-derived acyl group include a dialkylphosphonyl group such as dimethylphosphonyl and the like, a diarylphosphonyl group such as diphenylphosphonyl and the like.

The above-exemplified acyl groups may be further substituted with the aforementioned hydrocarbon group, heterocyclic group or the like at least one position of the acyl group.

Examples of the alkoxycarbonyl group optionally having substituent(s) include an alkoxycarbonyl group and a substituted alkoxycarbonyl group. The alkoxycarbonyl group is, for example, an alkoxycarbonyl group of 2 to 20 carbon atoms, which may be straight-chain, branched or cyclic, and examples of such alkoxycarbonyl group include methoxycarbonyl, ethoxycarbonyl, n-propoxycarbonyl, isopropoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, and the like. Examples of the substituent include the aforementioned alkyl group, aryl group, halogen atom, heterocyclic group, alkoxy group, and the like.

Examples of the aryloxycarbonyl group optionally having substituent(s) include an aryloxycarbonyl group and a substituted aryloxycarbonyl group. The aryloxycarbonyl group is, for example, an aryloxycarbonyl group of 7 to 20 carbon atoms and specific examples of such aryloxycarbonyl group include phenoxycarbonyl, naphthyloxycarbonyl, and the like. Examples of the substituent on the aryl group include the aforementioned alkyl group, aryl group, alkoxy group, halogen atom, and the like.

Examples of the carbamoyl group optionally having substituent(s) include a carbamoyl group and a substituted carbamoyl group. Examples of the substituted carbamoyl group include a carbamoyl group in which one or two hydrogen atom(s) of the amino group in the carbamoyl group are substituted with substituent(s) such as a hydrocarbon group optionally having substituent(s) and the like. The hydrocarbon group optionally having substituent(s) may be the same as the hydrocarbon group optionally having substituent(s) explained above. Specific examples of the substituted carbamoyl group include N-methylcarbamoyl, N,N-diethylcarbamoyl, N-phenylcarbamoyl group, and the like.

Examples of the alkylthiocarbonyl group optionally having substituent(s) include an alkylthiocarbonyl group and a substituted alkylthiocarbonyl group. The alkylthiocarbonyl group is, for example, an alkylthiocarbonyl group of 2 to 20 carbon atoms, which may be straight-chain, branched or cyclic, and specific examples of such alkylthiocarbonyl group include methylthiocarbonyl, ethylthiocarbonyl, n-propylthiocarbonyl, isopropylthiocarbonyl, n-butylthiocarbonyl, tert-butylthiocarbonyl, pentylthiocarbonyl, hexylthiocarbonyl, 2-ethylhexylthiocarbonyl, laurylthiocarbonyl, stearylthiocarbonyl, cyclohexylthiocarbonyl, and the like.

Examples of the arylthiocarbonyl group optionally having substituent(s) include an arylthiocarbonyl group and a substituted arylthiocarbonyl group. The arylthiocarbonyl group is, for example, an arylthiocarbonyl group of 7 to 20 carbon atoms, and specific examples of such arylthiocarbonyl group include phenylthiocarbonyl, naphthylthiocarbonyl, and the like.

Examples of the alkylthio group optionally having substituent(s) include an alkylthio group and a substituted alkylthio group. The alkylthio group is, for example, an alkylthio group of 1 to 20 carbon atom(s), which may be straight-chain, branched or cyclic, and specific examples of such alkylthio group include methylthio, ethylthio, n-propylthio, isopropylthio, n-butylthio, 2-butylthio, isobutylthio, tert-butylthio, pentylthio, hexylthio, cyclohexylthio, and the like. Inter alia, the alkylthio group is preferably an alkylthio group of 1 to 10 carbon atom(s), more preferably an alkylthio group of 1 to 6 carbon atom(s).

Examples of the arylthio group optionally having substituent(s) include an arylthio group and a substituted arylthio group. The arylthio group is, for example, an arylthio group of 6 to 20 carbon atoms, and specific examples of such arylthio group include phenylthio, naphthylthio, and the like. Inter alia, the arylthio group is preferably an arylthio group of 6 to 14 carbon atoms.

Examples of the substituted amino group include an amino group in which one or two hydrogen atom(s) of the amino group is/are substituted with substituent(s) such as a protective group and the like. As the protective group, any one can be used as far as it is used as an amino protective group, and specific examples of such substituted amino group include the groups described as an amino protective group in "PROTECTIVE GROUPS IN ORGANIC SYNTHESIS THIRD EDITION (JOHN WILEY & SONS, INC. (1999)". Examples of the amino protective group include a hydrocarbon group (e.g. alkyl group, aryl group, aralkyl group, etc.) optionally having substituent(s), an acyl group, an alkoxycarbonyl group optionally having substituent(s), an aryloxycarbonyl group optionally having substituent(s), an aralkyloxycarbonyl group optionally having substituent(s), and the like. The hydrocarbon group optionally having substituent(s), the acyl group, the alkoxycarbonyl group optionally having substituent(s), the aryloxycarbonyl group optionally having substituent(s) and the aralkyloxycarbonyl group optionally having substituent(s) may be the same as respective groups explained in the protective group.

Examples of the amino group substituted with an alkyl group, i.e. an alkyl-substituted amino group, include a mono- or di-alkylamino group such as N-methylamino, N,N-dimethylamino, N,N-diethylamino, N,N-diisopropylamino, N-methyl-N-isopropylamino, N-cyclohexylamino, and the like.

Examples of the amino group substituted with an aryl group, i.e., an aryl-substituted amino group, include a mono- or di-arylamino group such as N-phenylamino, N,N-diphenylamino, N-naphthylamino, N-naphthyl-N-phenylamino, and the like.

Examples of the amino group substituted with an aralkyl group, i.e., an aralkyl-substituted amino group, include a mono- or di-aralkylamino group such as N-benzylamino, N,N-dibenzylamino, and the like.

In addition, further examples of such substituted amino group include a di-substituted amino group such as N-methyl-N-phenylamino, N-benzyl-N-methylamino, and the like.

Examples of the amino group substituted with an acyl group, i.e., an acylamino group, include formylamino, acetylamino, propionylamino, pivaloylamino, pentanoylamino, hexanoylamino, benzoylamino, —NHSO$_2$CH$_3$, —NHSO$_2$C$_6$H$_5$, —NHSO$_2$C$_6$H$_4$CH$_3$, —NHSO$_2$CF$_3$, —NHSO$_2$N(CH$_3$)$_2$, and the like.

Examples of the amino group substituted with an alkoxycarbonyl group, i.e., an alkoxycarbonylamino group, include methoxycarbonylamino, ethoxycarbonylamino, n-propoxycarbonylamino, n-butoxycarbonylamino, tert-butoxycarbonylamino, pentyloxycarbonylamino, hexyloxycarbonyloxy, and the like.

Examples of the amino group substituted with an aryloxycarbonyl group, i.e., an aryloxycarbonylamino group, include an amino group in which one hydrogen atom of the amino group is substituted with an aryloxycarbonyl group, and embodiments of such amino group include phenoxycarbonylamino, naphthyloxycarbonylamino, and the like.

Examples of the amino group substituted with an aralkyloxycarbonyl group, i.e., an aralkyloxycarbonylamino group, include benzyloxycarbonylamino, and the like.

Examples of the substituted silyl group include a tri-substituted silyl group in which three hydrogen atoms of the silyl group are substituted with substituents such as alkyl group, substituted alkyl group, aryl group, substituted aryl group, aralkyl group, substituted aralkyl group, alkoxy group, substituted alkoxy group, and the like. The alkyl group, the substituted alkyl group, the aryl group, the substituted aryl group, the aralkyl group, the substituted aralkyl group, the alkoxy group, and the substituted alkoxy group may be the same as respective groups explained above. Examples of the substituted silyl group include trimethylsilyl, triethylsilyl, triisopropylsilyl, tert-butyldimethylsilyl tert-butylmethoxyphenylsilyl, tert-butoxydiphenylsilyl, and the like.

Examples of the biaryl skeleton in the compounds represented by the formula (1) of the present invention include biphenyldiyl, binaphthalenediyl, phenylpyridyl and bipyridyl, and the like, which are a group capable of taking an axial chirality in the structure, and these groups may be optically active or inactive. As the biphenyldiyl group and the binaphthalenediyl group, a 1,1'-biaryl-2,2'-diyl type is preferable, and the biphenyldiyl group and the binaphthalenediyl group may be substituted with the aforementioned alkyl group, aryl group, heterocyclic group, alkoxy group, hydroxy group, amino group or substituted amino group, or the like.

Then, the biaryl group will be explained specifically.

Examples of the binaphthalenediyl group include a group of the following structure (11):

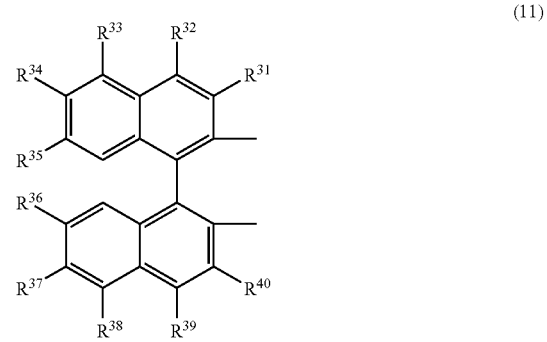

(wherein R$^{31}$ to R$^{40}$ each independently represent a hydrogen atom, a hydrocarbon group optionally having substituent(s), a heterocyclic group optionally having substituent(s), a hydroxy group, an alkoxy group optionally having substituent(s), an aryloxy group optionally having substituent(s), an acyl group, an alkoxycarbonyl group optionally having substituent(s), an aryloxycarbonyl group optionally having substituent(s), a carbamoyl group optionally having substituent(s), an alkylthiocarbonyl group optionally having substituent(s), an arylthiocarbonyl group optionally having substituent(s), a carboxyl group, an alkylthio group optionally having substituent(s), an arylthio group optionally having substituent(s), an amino group or a substituted amino group, a substituted silyl group or a halogen atom), and this may have an axial chirality in its structure. Examples of the hydrocarbon group optionally having substituent(s), the heterocyclic group optionally having substituent(s), the alkoxy group optionally having substituent(s), the aryloxy group optionally having substituent(s), the acyl group, the alkoxycarbonyl group optionally having substituent(s), the aryloxycarbonyl group optionally having substituent(s), the carbamoyl group optionally having substituent(s), the alkylthiocarbonyl group optionally having substituent(s), the arylthiocarbonyl group optionally having substituent(s), the alkylthio group optionally having substituent(s), the arylthio group optionally having substituent(s), the amino group or the substituted amino group, the substituted silyl group and the halogen atom include those described above.

Examples of the biphenyldiyl group include a group of the following structure (12):

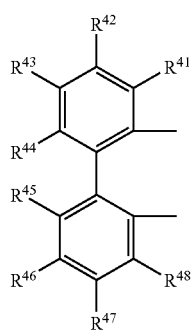

(12)

(wherein $R^{41}$ to $R^{48}$ each independently represent a hydrogen atom, a hydrocarbon group optionally having substituent(s), a heterocyclic group optionally having substituent(s), a hydroxy group, an alkoxy group optionally having substituent(s), an aryloxy group optionally having substituent(s), an acyl group, an alkoxycarbonyl group optionally having substituent(s), an aryloxycarbonyl group optionally having substituent(s), a carbamoyl group optionally having substituent(s), an alkylthioboarbonyl group optionally having substituent(s), an arylthiocarbonyl group optionally having substituent(s), a carboxyl group, an alkylthio group optionally having substituent(s), an arylthio group optionally having substituent(s), an amino group or a substituted amino group, a substituted silyl group or a halogen atom, or two of $R^{42}$, $R^{43}$ and $R^{44}$ may form an alkylene group optionally having substituent(s) or an alkylenedioxy group optionally having substituent(s), or two of $R^{45}$, $R^{46}$ and $R^{47}$ may form an alkylene group optionally having substituent(s) or an alkylenedioxy group optionally having substituent(s), provided that $R^{44}$ and $R^{45}$ are not a hydrogen atom, or $R^{44}$ and $R^{45}$ may form an alkylene group or an alkylenedioxy group), and this may have an axial chirality in its structure.

In addition, examples of the hydrocarbon group optionally having substituent(s), the heterocyclic group optionally having substituent(s), the alkoxy group optionally having substituent(s), the aryloxy group optionally having substituent(s), the acyl group, the alkoxycarbonyl group optionally having substituent(s), the aryloxycarbonyl group optionally having substituent(s), the carbamoyl group optionally having substituent(s), the alkylthiocarbonyl group optionally having substituent(s), the arylthiocarbonyl group optionally having substituent(s), the alkylthio group optionally having substituent(s), the arylthio group optionally having substituent(s), the amino group or the substituted amino group, the substituted silyl group and the halogen atom in $R^{41}$ to $R^{48}$ include those described above.

When two of $R^{42}$, $R^{43}$ and $R^{44}$ form an alkylene group, and when two of $R^{45}$, $R^{46}$ and $R^{47}$ form an alkylene group, an alkylene group of 2 to 4 carbon atoms is preferable as the alkylene group, and specific examples of such alkylene group include ethylene, trimethylene and tetramethylene. Examples of the substituent of the alkylene group optionally having substituent(s) include an alkyl group and a halogen atom, and the like, and specific examples of such alkyl group include methyl, ethyl, isopropyl, tert-butyl, and the like. Examples of the halogen atom include those described above.

When two of $R^{42}$, $R^{43}$ and $R^{44}$ form an alkylenedioxy group optionally having substituent(s), and when two of $R^{45}$, $R^{46}$ and $R^{47}$ form an alkylenedioxy group optionally having substituent(s), the alkylene moiety is preferably an alkylene group of 1 to 3 carbon atom(s), and specific examples include methylene, ethylene and trimethylene. In addition, when $R^{44}$ and $R^{45}$ form an alkylenedioxy group, the alkylene moiety is preferably an alkylene group of 1 to 6 carbon atom(s) is preferable, and specific examples of the alkylene moiety include methylene, ethylene, trimethylene, tetramethylene, pentamethylene, hexamethylene. Examples of the substituent for the alkylenedioxy group include an alkyl group and a halogen atom, and the like, and specific examples of such alkyl group include methyl, ethyl, isopropyl, tert-butyl, and the like, and examples of the halogen atom include a fluorine atom.

Examples of the phenylpyridyl group include a group of the following structures (13a) to (13d):

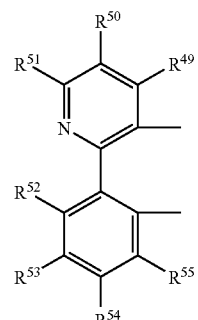

(13a)

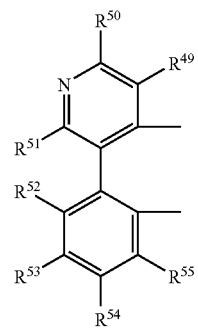

(13b)

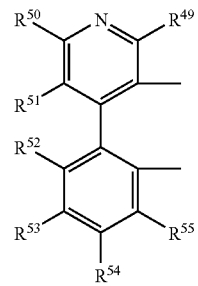

(13c)

-continued

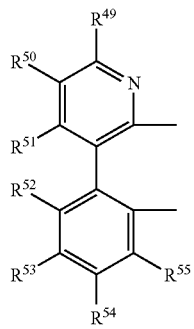

(13d)

wherein $R^{49}$ to $R^{55}$ each independently represent a hydrogen atom, a hydrocarbon group optionally having substituent(s), a heterocyclic group optionally having substituent(s), a hydroxy group, an alkoxy group optionally having substituent(s), an aryloxy group optionally having substituent(s), an acyl group, an alkoxycarbonyl group optionally having substituent(s), an aryloxycarbonyl group optionally having substituent(s), a carbamoyl group optionally having substituent(s), an alkylthiocarbonyl group optionally having substituent(s), an arylthiocarbonyl group optionally having substituent(s), a carboxyl group, an alkylthio group optionally having substituent(s), an arylthio group optionally having substituent(s), an amino group or a substituted amino group, a substituted silyl group or a halogen atom), and these may have an axial chirality in the structure.

In addition, examples of the hydrocarbon group optionally having substituent(s), the heterocyclic group optionally having substituent(s), the alkoxy group optionally having substituent(s), the aryloxy group optionally having substituent(s), the acyl group, the alkoxycarbonyl group optionally having substituent(s), the aryloxycarbonyl group optionally having substituent(s), the carbamoyl optionally having substituent(s), the alkylthiocarbonyl group optionally having substituent(s), the arylthiocarbonyl group optionally having substituent(s), the alkylthio group optionally having substituent(s), the arylthio group optionally having substituent(s), the amino group or the substituted amino group, the substituted silyl group and the halogen atom in $R^{49}$ to $R^{55}$ include those described above.

Examples of the bipyridyl group include a group in which one of the carbon atoms of the phenyl group is substituted with a nitrogen atom, in the structures (13a) to (13d).

The compound represented by the formula (1) can be prepared by the known method or the known per se method. For example, in the case of the compound having a binaphthalenediyl skeleton, such compound can be obtained by trifluoromethanesulfonylation of the hydroxy groups of a 2,2'-binaphthol with trifluoromethanesulfonic anhydride; reacting an alkylmagnesium halide such as methylmagnesium iodide with the trifluoromethanesulfonylated compound in the presents of a nickel catalyst to perform a coupling reaction; thereafter, effecting radical bromination on the alkyl group to obtain a 2'2'-bis(bromomethyl)-1,1'-binaphthyl derivative; and reacting the derivative with guanidine according to the description of J. Am. Chem. Soc., 2003, 125, 5139-5151 or JP-A No. 2001-48866.

(For convenience, the case where there is no substituent is explained, though not limited to)

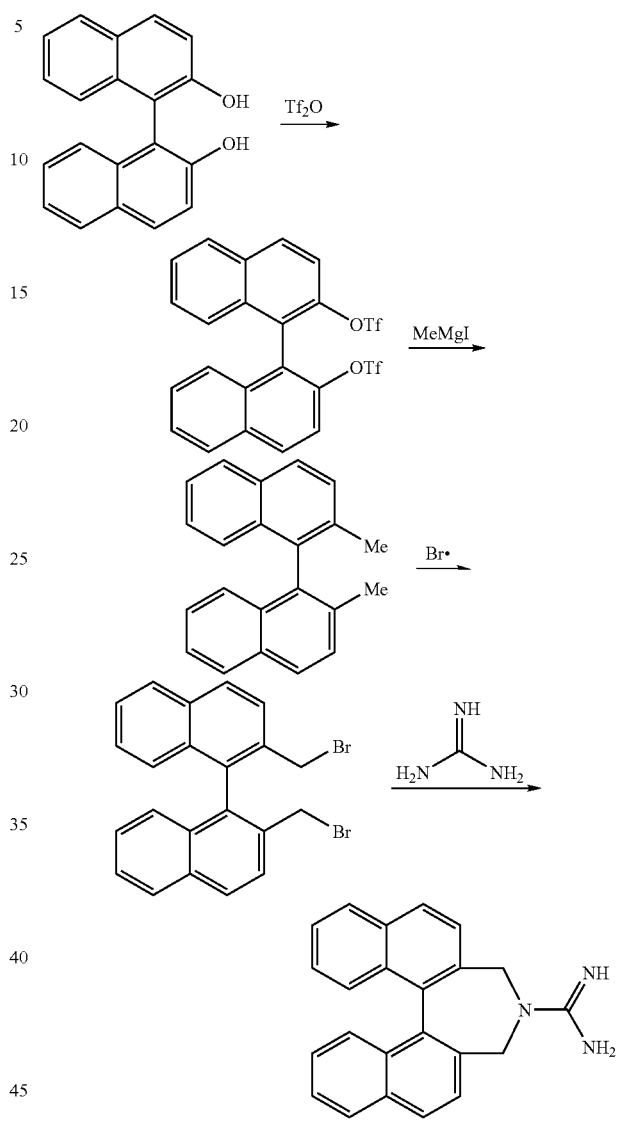

The guanidine compound represented by the formula (1) of the present invention is obtained by reacting the aforementioned dibromo form with preferably 1 to 20 equivalents, more preferably 1 to 10 equivalents, of guanidine in an alcohol solvent such as methanol, ethanol, n-propanol, isopropanol, n-butanol, tert-butanol, and the like, an ether solvent such as diethyl ether, diisopropyl ether, tetrahydrofuran (THF), and the like, or a mixed solvent of alcohol solvent and ether solvent.

The reaction is performed at a reaction temperature which is a suitable temperature between −20° C. to the boiling point of a solvent to be used, preferably 20° C. to 80° C., preferably for 30 minutes to 12 hours, more preferably for 1 to 11 hours while stirring.

After completion of the reaction, by performing suitable post-treatment, the guanidine compound of the present invention can be obtained.

In the present invention, the asymmetric nucleophilic addition reaction of a compound having at least one hydrogen atom on the carbon atom adjacent to an electron-withdrawing group or a nucleophilic agent with a carbonyl compound or an imine compound is performed by using an optically active guanidine compound represented by the formula (1) of the present invention. Examples of the carbonyl compound or the imine compound referred herein include a compound represented by the following formula (2):

$$R^{16}(C\!\!=\!\!Y)R^{17} \qquad (2)$$

(wherein $R^{16}$ and $R^{17}$ each independently represent a hydrogen atom, a hydrocarbon group optionally having substituent(s) or a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s) or a carbamoyl group optionally having substituent(s); Y represents an oxygen atom or $NR^{18}$ wherein $R^{18}$ represents a hydrogen atom, a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), a carbamoyl group optionally having substituent(s) or an amino group optionally having substituent(s)), and examples of the hydrocarbon group optionally having substituent(s), the heterocyclic group optionally having substituent(s), the acyl group, the alkoxycarbonyl group optionally having substituent(s), the aryloxycarbonyl group optionally having substituent(s), the alkylthiocarbonyl group optionally having substituent(s), the arylthiocarbonyl group optionally having substituent(s) or the carbamoyl group optionally having substituent(s) in the formula (2) include those describe above.

Examples of the compound having at least one hydrogen atom on the carbon atom adjacent to an electron-withdrawing group include a compound represented by the following formula (3):

$$R^{19}R^{20}CHQ^{1} \qquad (3)$$

(wherein $R^{19}$ and $R^{20}$ each independently represent a hydrogen atom, a hydrocarbon group optionally having substituent(s), a heterocyclic group optionally having substituent(s), an alkoxy group optionally having substituent(s), a hydroxy group, an amino group, a substituted amino group, an alkylthio group optionally having substituent(s), an arylthio group optionally having substituent(s), an acyl group, an alkoxycarbonyl group optionally having substituent(s), an alkylthiocarbonyl group optionally having substituent(s), an aryloxycarbonyl group optionally having substituent(s), an arylthiocarbonyl group optionally having substituent(s), a carbamoyl group optionally having substituent(s), a substituted imino group, a cyano group, a nitro group or a halogen atom, and $Q^1$ represents an electron-withdrawing group), and the hydrocarbon group optionally having substituent(s), the heterocyclic group optionally having substituent(s), the alkoxy group optionally having substituent(s), the hydroxy group, the amino group, the substituted amino group, the alkylthio group optionally having substituent(s), the arylthio group optionally having substituent(s), the acyl group, the alkoxycarbonyl group optionally having substituent(s), the alkylthiocarbonyl group optionally having substituent(s), the aryloxycarbonyl group optionally having substituent(s), the arylthiocarbonyl group optionally having substituent(s), and the carbamoyl group optionally having substituent(s) in the formula (3) include those described above.

In the compound of the formula (3), the electron-withdrawing group $Q^1$ include groups having a positive a value in the Hammett rule, such as a nitro group, a cyano group, an acyl group, an alkoxycarbonyl group optionally having substituent(s), a carbamoyl group optionally having substituent(s) and the like. Specific examples of these groups include those described above.

Examples of the compound having at least one hydrogen atom on the carbon atom adjacent to an electron-withdrawing group are not limited to, but include malonic acid diesters such as dimethyl malonate, diethyl malonate, and the like; α,γ-diketones such as 2,4-pentanedione, dibenzoylmethane, 1,3-cyclohexanedione, and the like; β-ketoesters such as ethyl 3-oxobutyrate, methyl benzoylacetate, and the like; nitroalkanes such as nitromethane, nitroethane, and the like; cyanoalkanes such as acetonitrile, propionitrile, butyronitrile, benzyl cyanide, and the like; phosphites; iminoacetic acid esters; and the like.

In addition, as the nucleophilic agent, any one can be used as far as it is a compound which can generate a cyanide ion or a phosphonate anion, and examples of the compound which can generate a cyanide ion include metal cyanides such as sodium cyanide, potassium cyanide, copper cyanide, and the like, and silyl cyanides such as trimethylsilyl cyanide, and the like, and examples of the compound which can generate a phosphonate anion include dialkyl phosphites such as dimethyl phosphite, diethyl phosphite, diisopropyl phosphate, and the like; diaryl phosphates such as diphenyl phosphite, ditolyl phosphite, and the like; hydroxydialkylphosphines such as hydroxydimethylphosphine, hydroxydiethylphosphine, hydroxydiisopropylphosphine, hydroxydi(n-butyl)phosphine, and the like; hydroxydiarylphosphines such as hydroxydiphenylphosphine, hydroxydi(p-tolyl)phosphine, hydroxydi(p-anisyl)phosphine, and the like.

In the asymmetric nucleophilic addition reaction of the present invention, as the compound represented by the formula (2) used as a raw material, and the compound having an electron-withdrawing group represented by the formula (3) and the nucleophilic agent, it may be possible to use commercially available products as they are, or to use those obtained by appropriately purifying these products, if necessary, or to use those prepared in-house by the known per se general process.

The asymmetric nucleophilic addition reaction of the present invention can be preferably performed by stirring an optically active compound represented by the formula (1), a compound having an electron-withdrawing group represented by the formula (3) or a nucleophilic agent and a compound represented by the formula (2) at a suitable reaction temperature for a suitable reaction time.

The present reaction can be performed under atmospheric air, and may be performed in an inert gas such as nitrogen or argon.

The amount of the compound having an electron-withdrawing group represented by the formula (3) to be used is sufficiently 0.5-fold mole to 20-fold moles, preferably 1.0-fold mole to 5.0-fold moles relative to the amount of the compound represented by formula (2).

The amount of the compound represented by the formula (1) is sufficiently 0.1-mol % to 50 mol %, preferably 1 mol % to 20 mol %, more preferably 5 mol % to 10 mol % relative to amount of the compound represented by the formula (2).

The reaction solvent is not particularly limited as far as it is not involved in the reaction, for examples, amides such as N,N-dimethylformamide, formamide, N,N-dimethylacetamide, and the like; halogenated hydrocarbons such as dichloromethane, 1,2-dichloroethane, chloroform, carbon tetrachloride, o-dichlorobenzene, and the like; aliphatic hydrocarbons such as pentane, hexane, heptane, octane, decane, cyclohexane, and the like; aromatic hydrocarbons such as benzene, toluene, xylene, and the like; alcohols such as methanol, ethanol, tert-butanol, and the like; ethers such as diethyl ether, diisopropyl ether, tert-butyl methyl ether, dimethoxyethane, ethylene glycol diethyl ether, tetrahydrofuran, 1,4-dioxane, 1,3-dioxolane, and the like; sulfoxides such as dimethyl sulfoxide, and the like. Among these solvents, ethers such as tetrahydrofuran, diethyl ether, and the like, and halogenated hydrocarbons such as dichloromethane and the like are preferable. These solvents may be used alone or in appropriate combination with two or more solvents.

The reaction temperature is naturally different depending on a substrate to be used, and usually in a range of −100° C. to 100° C., preferably −100 to 0° C.

The reaction time is naturally different depending on a substrate to be used, and is usually 1 hour to 100 hours, preferably 3 hours to 80 hours.

After completion of the reaction, suitable treatment is performed, and the reaction solution is extracted with a suitable solvent. After removal of the solvent by evaporation, an objective optically active alcohol can be obtained by procedures such as crystallization, distillation and various chromatographies alone or in combination thereof.

In the present invention, the asymmetric Michael addition reaction of a compound having at least one hydrogen atom on the carbon atom adjacent to an electron-withdrawing group or a nucleophilic agent with an α,β-unsaturated compound is performed by using an optically active form of the guanidine compound represented by the formula (1) of the present invention. The α,β-unsaturated compound referred herein has an unsaturated bond between the α-carbon atom and the β-carbon atom counting from the position of an electron-withdrawing group (definition of the electron-withdrawing group is according to $Q^1$), and examples of α,β-unsaturated compound include an α,β-unsaturated carbonyl compound represented by the following formula (4):

$$R^{23}R^{24}C=CR^{25}Q^2 \qquad (4)$$

(wherein $R^{23}$ to $R^{25}$ each independently represent a hydrogen atom, a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), a carbamoyl group optionally having substituent(s), a cyano group, a nitro group, a halogen atom, an alkoxy group optionally having substituent(s), an aryloxy group optionally having substituent(s), an alkylthio group optionally having substituent(s) or an arylthio group optionally having substituent(s); and $Q^2$ represents an electron-withdrawing group, and in any combination of $R^{23}$ to $R^{25}$ and $Q^2$, these substituents may be taken together to form a ring); and examples of the hydrocarbon group optionally having substituent(s), the heterocyclic group optionally having substituent(s), the acyl group, the alkoxycarbonyl group optionally having substituent(s), the aryloxycarbonyl group optionally having substituent(s), the alkylthiocarbonyl group optionally having substituent(s), the arylthiocarbonyl group optionally having substituent(s), the carbamoyl group optionally having substituent(s), the halogen atom, the alkoxy group optionally having substituent(s), the aryloxy group optionally having substituent(s), the alkylthio group optionally having substituent(s) or the arylthio group optionally having substituent(s) include those described above.

Alternatively, $R^{23}$ to $R^{25}$ and $Q^2$ may form a ring, and the general skeleton of the compound may take a cycloalkenone skeleton such as cyclopentenone and cyclohexenone. Definition of $Q^2$ is according to the definition of $Q^1$, and examples of $Q^2$ include a nitro group, a cyano group, an acyl group, an alkoxycarbonyl group optionally having substituent(s), a carbamoyl group optionally having substituent(s) and the like, and specific examples of these groups include those describe above.

In addition, the compound having at least one hydrogen atom on the carbon atom adjacent to an electron-withdrawing group is, for example, an active methylene compound, including specifically malonic acid diesters, diketones, β-ketoesters, nitroalkanes, cyanoalkanes, iminoacetic acid esters, and the like though they are not limited to, but include specifically those describe above.

Examples of the nucleophilic agent include a compound represented by the following formula (6):

$$R^{26}ZH \qquad (6)$$

wherein Z represents an oxygen atom, a sulfur atom, or a nitrogen atom optionally having substituent(s); when Z represents an oxygen atom or a sulfur atom, $R^{26}$ represents a hydrogen atom, a hydrocarbon group optionally having substituent(s), a heterocyclic group optionally having substituent(s), an amino group optionally having substituent(s), an acyl group or a cyano group; when Z represents a nitrogen atom optionally having substituent(s), $R^{26}$ represents a hydrogen atom, a hydrocarbon group optionally having substituent(s), a heterocyclic group optionally having substituent(s), an alkoxy group optionally having substituent(s), an aryloxy group optionally having substituent(s), an amino group optionally having substituent(s), an acyl group, an alkoxycarbonyl group optionally having substituent(s), an aryloxycarbonyl group optionally having substituent(s), or a carbamoyl group optionally having substituent(s)), a cyanide, an azide, a phosphonate and a hydroxy-di-substituted phosphine (HP(=O)$(R^{21})_2$ or HOP$(R^{21})_2$, wherein $R^{21}$ represents a hydrocarbon group optionally having substituent(s), a heterocyclic group optionally having substituent(s), an alkoxy group optionally having substituent(s), an aryloxy group optionally having substituent(s), a thioalkoxy group optionally having substituent(s) or a thioaryloxy group optionally having substituent(s)), and examples of the hydrocarbon group optionally having substituent(s), the heterocyclic group optionally having substituent(s), the alkoxy group optionally having substituent(s), the aryloxy group optionally having substituent(s), the amino group optionally having substituent(s), the acyl group, the alkoxycarbonyl group optionally having substituent(s), the aryloxycarbonyl group optionally having substituent(s), the alkylthiocarbonyl group optionally having substituent(s), the arylthiocarbonyl group optionally having substituent(s), or the carbamoyl group optionally having substituent(s) include those described above.

Herein, examples of the compound represented by the formula (6) include an oxygen-containing compound having a reactive hydroxy group, such as alcohols, phenols, and the like, a sulfur compound having a reactive mercapto group, such as alkanethiols, arylthiols, and the like, and a nitrogen-containing compound having at least one hydrogen atom on the amino group.

Examples of the cyanide, the azide and the phosphonate include compounds which can generate a cyanide ion, an azide ion or a phosphonate anion, and examples of the compound which can generate a cyanide ion include a metal cyanide such as sodium cyanide, potassium cyanide, copper cyanide, and the like, a silyl cyanides such as trimethylsilyl cyanide, and the like. Examples of the compound which can generate an azide ion include azides such as sodium azide, trimethylsilyl azide, and the like, and examples of the compound which can generate a phosphonate anion include dialkyl phosphates such as dimethyl phosphate, diethyl phosphite, diisopropyl phosphite, and the like; diaryl phosphates such as diphenyl phosphate, ditolyl phosphite, and the like; hydroxydialkylphosphines such as hydroxydimethylphosphine, hydroxydiethylphosphine, hydroxydiisopropylphosphine, hydroxyl-di(n-butyl)phosphine, and the like; hydroxydiarylphosphines such as hydroxydiphenylphosphine, hydroxydi(p-tolyl)phosphine, hydroxydi(p-anisyl)phosphine, and the like.

In the asymmetric Michael addition reaction of the present invention, as the α,β-unsaturated compound used as a raw material, the compound having at least one hydrogen atom on the carbon atom adjacent to an electron-withdrawing group, and the nucleophilic agent, it may be possible to use commercially available products as they are, or to use products obtained by appropriately purifying those products, if necessary, or to use those prepared in-house by the known per se process.

In the asymmetric Michael addition reaction of the present invention, an asymmetric Michael-type reaction can be performed by stirring an optically active substance of the compound represented by the formula (1), a nucleophilic agent and an α,β-unsaturated compound at a suitable temperature for a suitable reaction time.

The present reaction can be performed under atmospheric air, and may be performed in an inert gas such as nitrogen and argon.

The amount of each of the compound having at least one hydrogen atom on the carbon atom adjacent to an electron-withdrawing group and the nucleophilic agent to be used is sufficiently 0.5-fold mole to 20-fold moles, preferably 1-fold mole to 5-fold moles relative to the amount of the α,β-unsaturated compound.

The amount of each of the compound represented by the formula (1) to be used is sufficiently 0.1 mol % to 50 mol %, preferably 1 mol % to 20 mol %, more preferably 5 mol % to 10 mol % relative to the amount of the α,β-unsaturated compound.

The reaction solvent is not particularly limited as far as it is not involved in the reaction, and examples of such solvent include amides such as N,N-dimethylformamide, formamide, N,N-dimethylacetamide, and the like; halogenated hydrocarbons such as dichloromethane, 1,2-dichloroethane, chloroform, carbon tetrachloride, o-dichlorobenzene, and the like; aliphatic hydrocarbons such as pentane, hexane, heptane, octane, decane, cyclohexane, and the like; aromatic hydrocarbons such as benzene, toluene, xylene, and the like; alcohols such as methanol, ethanol, tert-butanol, and the like; ethers such as diethyl ether, diisopropyl ether, tert-butyl methyl ether, dimethoxyethane, ethylene glycol diethyl ether, tetrahydrofuran, 1,4-dioxane, 1,3-dioxolane, and the like; and sulfoxides such as dimethyl sulfoxide and the like, and the like. The more preferable solvents include ethers such as tetrahydrofuran, diethyl ether, and the like, and halogenated hydrocarbons such as dichloromethane and the like. These solvents may be used alone or in appropriate combination of two or more solvents.

The reaction temperature naturally differs depending on a substrate to be used, and is usually in a range of −100° C. to 100° C., preferably −80° C. to 50° C.

The reaction time naturally differs depending on a substrate to be used, and is usually 1 hour to 100 hours, preferably 3 hours to 50 hours.

After completion of the reaction, suitable treatment is performed, and the reaction solution is extracted with a suitable solvent. After removal of the solvent from the extract, an objective Michael adduct can be obtained by procedures such as crystallization, distillation or various chromatographies or the like alone or in combination thereof.

In the present invention the asymmetric epoxidation reaction of a peroxy compound with an α,β-unsaturated compound is performed by using an optically active form of the guanidine compound represented by the formula (1) of the present invention. Examples of the α,β-unsaturated compound include compounds represented by the formula (4).

Examples of the peroxy compound include a compound represented by the formula (7):

$$R^{26}OOH \qquad (7)$$

(wherein $R^{26}$ represents a hydrogen atom, a hydrocarbon group optionally having substituent(s), a heterocyclic group optionally having substituent(s) or an acyl group), and examples of the hydrocarbon group optionally having substituent(s), the heterocyclic group optionally having substituent(s) or the acyl group include those described above.

Specific examples of the peroxy compound include hydrogen peroxide, peracetic acid, tert-butyl hydroperoxide and cumene peroxide, and the like. Alternatively, a solution in which the peroxy compound is dissolved in water or a suitable organic solvent can also be preferably used in the reaction of the present invention.

In the asymmetric epoxidation reaction of the present invention, as the α,β-unsaturated compound used as a raw material, it may be possible to use commercially available products as they are, or to use compounds obtained by appropriately purifying those products, if necessary, or to use compounds prepared in-house by the general process known per se.

In the asymmetric epoxidation reaction of the present invention, such asymmetric epoxidation reaction can be preferably performed by stirring an optical active form of the compound represented by the formula (1), a peroxy compound and an α,β-unsaturated compound at a suitable reaction temperature for a suitable reaction time.

The present reaction can be performed under atmospheric air.

It is sufficient to use the peroxy compound in an amount of 1.0-fold mole to 2-fold moles, preferably 1.0-fold mole to 1.5-fold moles relative to the amount of the α,β-unsaturated compound.

The amount of the compound represented by the formula (1) to be used is sufficiently 0.1 mol % to 50 mol %, preferably 1 mol % to 20 mol %, more preferably 5 mol % to 10 mol % relative to the amount of the α,β-unsaturated compound.

The reaction solvent is not particularly limited as far as it is not involved in the reaction, and examples of such solvents include amides such as N,N-dimethylformamide, formamide, N,N-dimethylacetamide, and the like; halogenated hydrocarbons such as dichloromethane, 1,2-dichloroethane, chloroform, carbon tetrachloride, o-dichlorobenzene, and the like; aliphatic hydrocarbons such as pentane, hexane, heptane, octane, decane, cyclohexane, and the like; aromatic hydrocarbons such as benzene, toluene, xylene, and the like;

alcohols such as methanol, ethanol, tert-butanol, and the like; ethers such as diethyl ether, diisopropyl ether, tert-butyl methyl ether, dimethoxyethane, ethylene glycol dimethyl ether, tetrahydrofuran, 1,4-dioxane, 1,3-dioxolane, and the like; and sulfoxides such as dimethyl sulfoxide and the like. Among these solvents, ethers such as tetrahydrofuran, diethyl ether, and the like, and halogenated hydrocarbons such as dichloromethane and the like are more preferable. These solvents may be used alone or in appropriate combination with two or more solvents.

The reaction temperature naturally differs depending on a substrate to be used, and is usually in a range of −80° C. to 80° C., preferably a range of −50° C. to 50° C.

The reaction time naturally differs depending on a substrate to be used, and is usually 1 hour to 80 hours, preferably 3 hours to 50 hours.

After completion of the reaction, suitable treatment is performed, and the reaction solution is extracted with a suitable solvent. After removal of the solvent from the extract, an objective epoxy form can be obtained by procedures such as crystallization, distillation and various chromatographies alone or in combination thereof.

A process for producing an optically active compound represented by the formula (9a) or (9b) using the asymmetric nucleophilic addition reaction of the present invention is performed by reacting a nitrogen-containing compound (8) and an active methylene compound or an active methyne compound (3) in the presence of an optically active form of a guanidine compound represented by the formula (1), as shown in the following scheme.

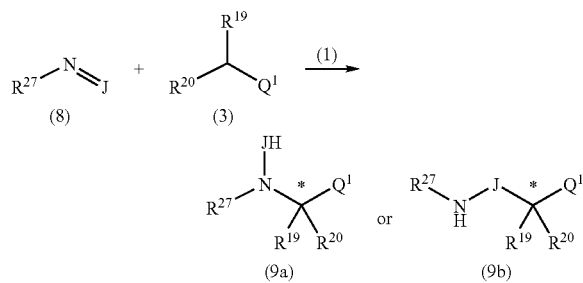

(in the scheme, $R^{27}$ represents a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), or a carbamoyl group optionally having substituent(s), and J represents an oxygen atom or $NR^{28}$ ($R^{28}$ represents a hydrocarbon group optionally having substituent(s), a heterocyclic group optionally having substituent(s), an acyl group, an alkoxycarbonyl group optionally having substituent(s), an aryloxycarbonyl group optionally having substituent(s), an alkylthiocarbonyl group optionally having substituent(s), an arylthiocarbonyl group optionally having substituent(s), or a carbamoyl group optionally having substituent(s)), * represents an asymmetric carbon atom, and $R^{19}$ and $R^{20}$ are the same as defined above).

Herein, examples of the hydrocarbon group optionally having substituent(s), the heterocyclic group optionally having substituent(s), the acyl group, the alkoxycarbonyl group optionally having substituent(s), the aryloxycarbonyl group optionally having substituent(s), the alkylthiocarbonyl group optionally having substituent(s), the arylthiocarbonyl group optionally having substituent(s), and the carbamoyl group optionally having substituent(s) include those described above.

Examples of the nitrogen-containing compound represented by the formula (8) include a nitroso compound and an azo compound, and specific examples of such compound are not limited to, but include nitroso compounds such as nitrosomethane, 2-methyl-2-nitrosopropane, nitrosobenzene, 2-nitrosotoluene, 4-nitrosophenol, 1-nitrosopyrrolidine, and the like, azo compounds such as azo-tert-butane, azobenzene, diethyl azodicarboxylate, 1,1'-(azodicarbonyl) dipiperidine, and the like.

Examples of the compound represented by the formula (3) include compounds described above.

In the process for producing the optically active compound as mentioned above, as the nitrogen-containing compound used as a raw material, and the active methylene compound or the active methyne compound, it may be possible to use commercially available products as they are, or to use compounds obtained by appropriately purifying those products, if necessary, or to use compounds prepared in-house by the general process known per se.

In the process for producing the optically active compounds, the reaction can be performed preferably by stirring an optically active form of the compound represented by the formula (1), an active methylene compound or an active methyne compound and a nitrogen-containing compound at a suitable reaction temperature for a suitable reaction time.

The present reaction can be performed under atmospheric air, and may be performed in an inert gas such as nitrogen or argon.

The amount of the active methylene compound or the active methyne compound to be used is sufficiently 1.0-fold mole to 3-fold moles, preferably 1.1-fold moles to 1.5-fold moles relative to the amount of the nitrogen-containing compound.

The amount of the compound represented by the formula (1) to be used is sufficiently 0.1 mol % to 50 mol %, preferably 1 mol % to 20 mol %, more preferably 3 mol % to 10 mol % relative to the amount of the nitrogen-containing compound.

The reaction solvent is not particularly limited as far as it is not involved in the reaction, and examples of such solvent include amides such as N,N-dimethylformamide, formamide, N,N-dimethylacetamide, and the like; halogenated hydrocarbons such as dichloromethane, 1,2-dichloroethane, chloroform, carbon tetrachloride, o-dichlorobenzene, and the like; aliphatic hydrocarbons such as pentane, hexane, heptane, octane, decane, cyclohexane, and the like; aromatic hydrocarbons such as benzene, toluene, xylene, and the like; alcohols such as methanol, ethanol, tert-butanol, and the like; ethers such as diethyl ether, diisopropyl ether, tert-butyl methyl ether, dimethoxyethane, ethylene glycol diethyl ether, tetrahydrofuran, 1,4-dioxane, 1,3-dioxolane, and the like; and sulfoxides such as dimethyl sulfoxide and the like. Among these solvents, amides such as N,N-dimethylformamide and N,N-dimethylacetamide, and dimethyl sulfoxide and the like are more preferable. These solvents may be used alone or in appropriate combination of two or more solvents.

The reaction temperature naturally differs depending on a substrate to be used, and is usually in a range of −100° C. to 50° C., preferably −50° C. to 30° C.

The reaction time naturally differs depending on a substrate to be used, and is usually 1 hour to 50 hours, preferably 3 hours to 30 hours.

After completion of the reaction, suitable treatment is performed, and the reaction solution is extracted with a suitable solvent. After removal of the solvent from the extract, an objective optically active compound can be obtained by procedures such as crystallization, distillation and various chromatographies alone or in combination thereof.

The process for producing an optically active compound by dissymmetric procedure using the Wittig reaction can be performed by reacting a carbonyl compound having a skeleton which has σ symmetry and forms an asymmetric carbon atom after the reaction, and a phosphorus compound (10) in the presence of an optically active form of the guanidine compound of the formula (1). Examples of the phosphorus compound used herein include a compound which can produce a phosphorus ylide with a base, represented by the formula (10).

$$R^{28}R^{29}CHP(=O)R^{30}R^{31} \qquad (10)$$

(wherein $R^{28}$ and $R^{29}$ each independently represent a hydrogen atom, a hydrocarbon group optionally having substituent(s), a heterocyclic group optionally having substituent(s), an alkoxy group optionally having substituent(s), a hydroxy group, a substituted amino group, an alkylthio group optionally having substituent(s), an acyl group, an alkoxycarbonyl group optionally having substituent(s), an alkylthiocarbonyl group optionally having substituent(s), a carbamoyl group optionally having substituent(s), a substituted imino group, a cyano group, a nitro group or a halogen atom, provided that $R^{28}$ and $R^{29}$ are not the same substituent simultaneously, and $R^{30}$ and $R^{31}$ each independently represent a hydrocarbon group optionally having substituent(s), a heterocyclic group optionally having substituent(s), an alkoxy group optionally having substituent(s) or an aryloxy group optionally having substituent(s)).

Examples of the hydrocarbon group optionally having substituent(s), the heterocyclic group optionally having substituent(s), the alkoxy group optionally having substituent(s), the substituted amino group, the alkylthio group optionally having substituent(s), the acyl group, the alkoxycarbonyl group optionally having substituent(s), the alkylthiocarbonyl group optionally having substituent(s), the carbamoyl group optionally having substituent(s), the substituted imino group or the halogen atom include those described above.

Examples of the carbonyl compound having a skeleton which has σ symmetry and forms an asymmetric carbon atom after the reaction include a cyclohexanone having substituent(s) at the 4-position, and examples of such substituent are not limited to, but include an alkyl group such as methyl, tert-butyl, and the like, an aryl group such as phenyl, tolyl, and the like, and an alkoxy group such as methoxy, tert-butoxy, and the like.

Herein, as the phosphorus compound and the carbonyl compound used as a raw material, commercially available products may be used as they are, or compounds obtained by appropriately purifying those products, if necessary, may be used, or compounds prepared by the general process known per se may be used.

In the process of the optically active compounds, the reaction can be performed preferably by stirring an optically active form of the compound represented by the formula (1), a phosphorus compound and a carbonyl compound at a suitable reaction temperature for a suitable reaction time.

The present reaction can be performed under atmospheric air, and may be performed in an inert gas such as nitrogen or argon.

The amount of the phosphorus compound to be used is sufficiently 1.0-fold mole to 3-fold moles, preferably 1.1-fold moles to 1.5-fold moles relative to the amount of the carbonyl compound.

The amount of the compound represented by the formula (1) to be used is sufficiently 0.1 mol % to 50 mol %, preferably 1 mol % to 20 mol %, more preferably 3 mol % to 10 mol % relative to the amount of the carbonyl compound.

The reaction solvent is not particularly limited as far as it is not involved in the reaction, and examples of such solvent include amides such as N,N-dimethylformamide, formamide, N,N-dimethylacetamide, and the like; halogenated hydrocarbons such as dichloromethane, 1,2-dichloroethane, chloroform, carbon tetrachloride, o-dichlorobenzene, and the like; aliphatic hydrocarbons such as hexane, heptane, octane, decane, cyclohexane, and the like; aromatic hydrocarbons such as benzene, toluene, xylene, and the like; alcohols such as methanol, ethanol, tert-butanol, and the like; ethers such as diethyl ether, diisopropyl ether, tert-butyl methyl ether, dimethoxyethane, ethylene glycol diethyl ether, tetrahydrofuran, 1,4-dioxane, 1,3-dioxolane, and the like; and sulfoxides such as dimethyl sulfoxide and the like. Among these solvents, amides such as N,N-dimethylformamide, N,N-dimethylacetamide, and the like, and dimethyl sulfoxide and the like are more preferable. These solvents may be used alone or in appropriate combination with two or more solvents.

The reaction temperature naturally differs depending on a substrate to be used, and is usually in a range of −50° C. to 50° C., preferably −30° C. to 30° C.

The reaction time naturally differs depending on a substrate to be used, and is usually 1 hour to 30 hours, preferably 3 hours to 15 hours.

After completion of the reaction, suitable treatment is performed, and the reaction solution is extracted with a suitable solvent. After removal of the solvent from the extract, an objective optically active compound can be obtained by procedures such as crystallization, distillation and various chromatographies or in combination thereof.

EXAMPLES

The present invention will be explained in more detail below by way of Examples, but the present invention is not limited by them.

Example 1

Synthesis of Guanidine Compound (A)

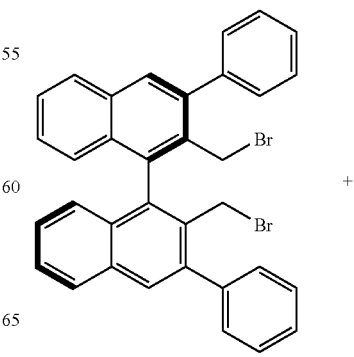

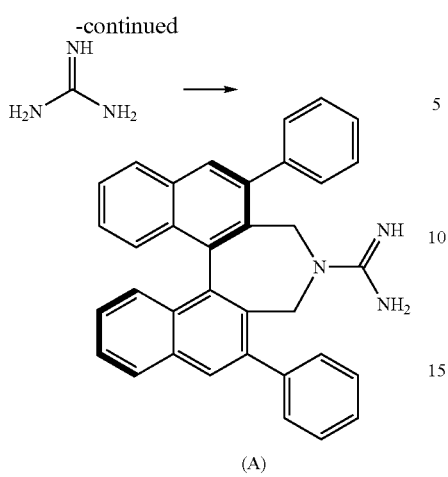

(A)

To a reaction vessel were added (R)-3,3'-bis(phenyl)-2,2'-bis(bromomethyl)-1,1'-binaphthyl (0.3 g, 0.5 mmol) and 5 mL of THF. Guanidine hydrochloride (0.48 g, 5.0 mmol) was neutralized (Amberlite IRA-400 (OH⁻), eluent: ethanol) to make a solution in 5 mL of ethanol, which was then added to the above THF solution, and the temperature was raised to 50° C. After disappearance of the dibromo form was confirmed on TLC, 1 mol/L hydrochloric acid was added. The reaction solution was extracted with methylene chloride, washed with water, and dried over anhydrous magnesium sulfate, and then the solvent was evaporated to obtain an objective hydrochloride. This hydrochloride was purified by silica gel column chromatography (ethyl acetate: methanol), and the resulting crystals were dissolved in methanol and neutralized with an ion exchange resin (Amberlite IRA-400 (OH⁻)). Removal of the solvent by evaporation gave an objective guanidine compound in 80% yield.

$^1$H-NMR (CDCl$_3$) δ: 8.00-7.94 (8H, m), 7.65-7.39 (14H, m), 7.28 (2H, t, J=7.3 Hz), 4.77 (2H, d, J=12.7 Hz), 3.62 (2H, d, J=12.7 Hz)

Examples 2 to 11

According to the same manner as that of Example 1, the following guanidine compounds (B) to (K) of the present invention were synthesized.

Example 2

Guanidine Compound (B): Yield 82%

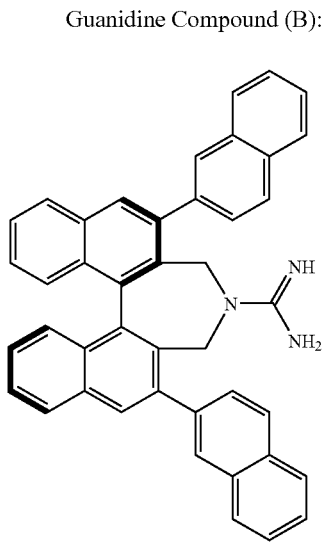

(B)

$^1$H-NMR (CDCl$_3$) δ: 8.07 (2H, s), 8.00-7.65 (10H, m), 7.63 (2H, d, J=8.4 Hz), 7.56-7.49 (8H, m), 7.33 (2H, dd, J=6.8, 8.4 Hz), 4.88 (2H, d, J=13.0 Hz), 3.73 (2H, d, J=13.0 Hz)

Example 3

Guanidine Compound (C): Yield 80%

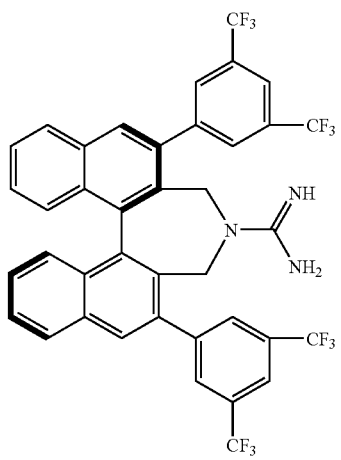

(C)

$^1$H-NMR (CDCl$_3$) δ: 8.00-7.93 (10H, m), 7.56 (2H, dd, J=6.8, 8.1 Hz), 7.46 (2H, d, J=6.5 Hz), 7.36 (2H, dd, J=6.5, 8.1 Hz), 4.62 (2H, d, J=13.0 Hz), 3.68 (2H, d, J=13.0 Hz)

Example 4

Guanidine Compound (D): Yield 65%

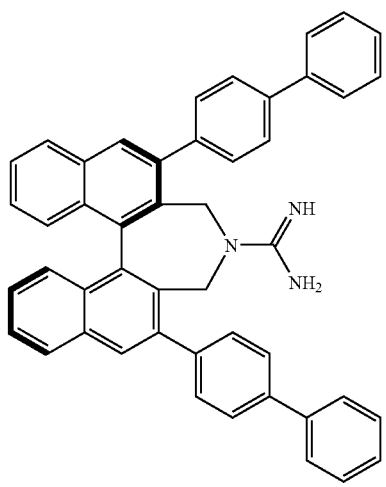

(D)

¹H-NMR (CDCl₃) δ: 8.02 (2H, s), 7.98 (2H, d, J=8.4 Hz), 7.73-7.17 (24H, m), 4.86 (2H, d, J=12.4 Hz), 3.69 (2H, d, J=12.4 Hz)
Example 5
Guanidine Compound (E): Yield 80%
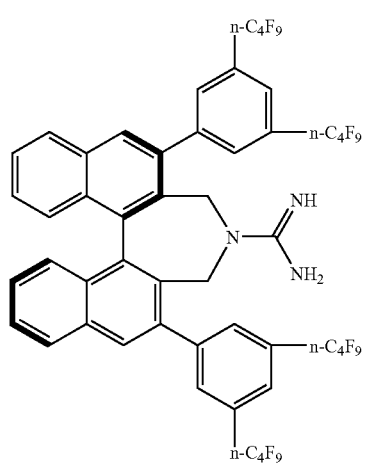
(E)
¹H-NMR (CDCl₃) δ: 8.02-7.95 (8H, m), 7.85 (2H, s), 7.60-7.48 (m, 4H), 7.38 (2H, dd, J=7.3, 8.6 Hz), 4.54 (2H, d, J=12.7 Hz), 3.67 (2H, d, J=12.7 Hz)
Example 6
Guanidine Compound (F): Yield 83%
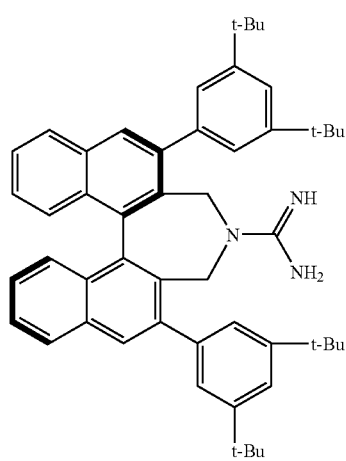
(F)
¹H-NMR (CDCl₃) δ: 7.99 (2H, s), 7.97 (2H, d, J=8.9 Hz), 7.55-7.48 (6H, m), 7.34-7.25 (6H, m), 4.74 (2H, d, J=13.2 Hz), 3.65 (2H, d, J=13.2 Hz), 1.37 (36H, s)
Example 7
Guanidine Compound (G): Yield 81%
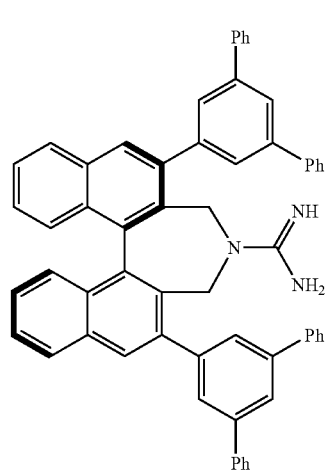
(G)
¹H-NMR (CDCl₃) δ: 8.09 (2H, s), 7.99 (2H, d, J=7.3 Hz), 7.86 (2H, s), 7.75-7.60 (10H, m), 7.58-7.32 (20H, m), 4.92 (2H, d, J=13.2 Hz), 3.80 (2H, d, J=13.2 Hz)
Example 8
Guanidine Compound (H): Yield 90%
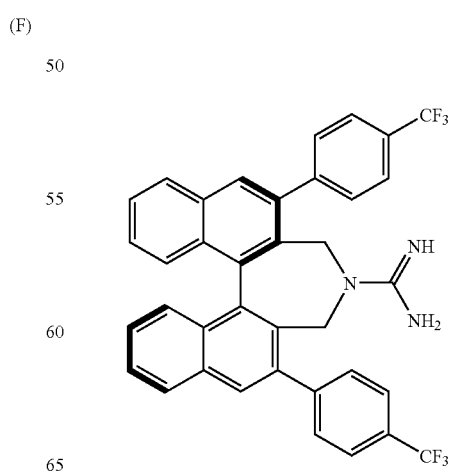
(H)

¹H-NMR (CDCl₃) δ: 7.97 (2H, d, J=6.8 Hz), 7.95 (2H, s), 7.73 (4H, d, J=7.8 Hz), 7.59-7.51 (6H, m), 7.45 (2H, d, J=8.1 Hz), 7.34 (2H, dd, J=6.8, 8.1 Hz), 4.69 (2H, d, J=13.0 Hz), 3.68 (2H, d, J=13.0 Hz)

Example 9

Guanidine Compound (I): Yield 72%

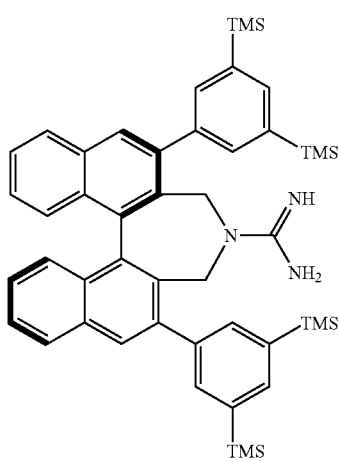

¹H-NMR (CDCl₃) δ: 7.96 (2H, d, J=6.8 Hz), 7.95 (2H, s), 7.69 (2H, s), 7.62 (4H, s), 7.54-7.46 (4H, m), 7.31 (2H, d, J=7.3 Hz), 4.75 (2H, br), 3.66 (2H, d, J=13.5 Hz), 0.30 (36H, s)

Example 10

Guanidine Compound (J): Yield 64%

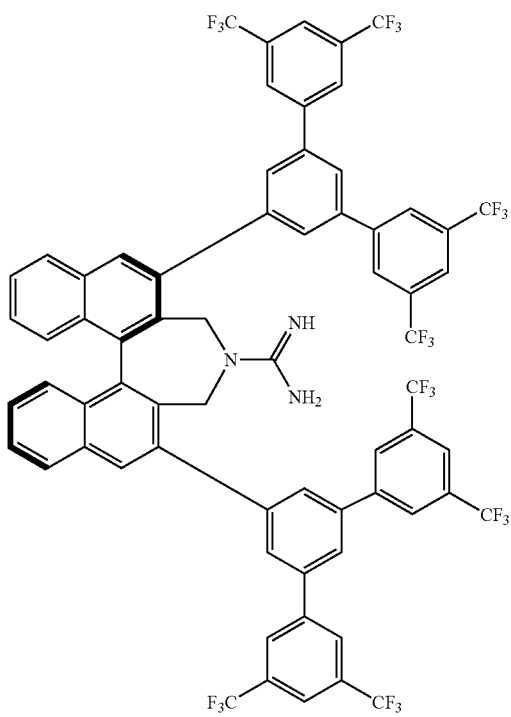

Example 11

Guanidine Compound (K): Yield 60%

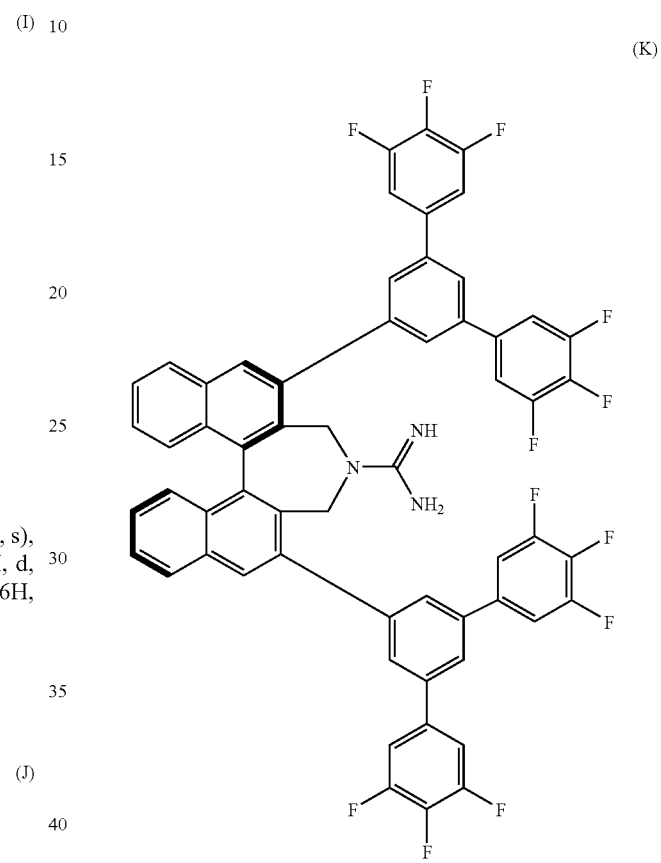

¹H-NMR (CDCl₃) δ: 8.16 (8H, s), 8.11 (2H, s), 8.01 (2H, d, J=8.4 Hz), 7.91 (4H, s), 7.84-7.76 (6H, m), 7.59-7.48 (4H, m), 5.03 (2H, br), 3.78 (2H, d, J=13.5 Hz)

¹H-NMR (CDCl₃) δ: 8.03 (2H, s) 7.99 (2H, d, J=8.1 Hz), 7.66 (6H, m), 7.56-7.48 (4H, m), 7.37-7.32 (10H, m), 4.87 (2H, br), 3.75 (2H, d, J=13.2 Hz)

Example 12

Asymmetric Nitroaldol Reaction (Henry Reaction)

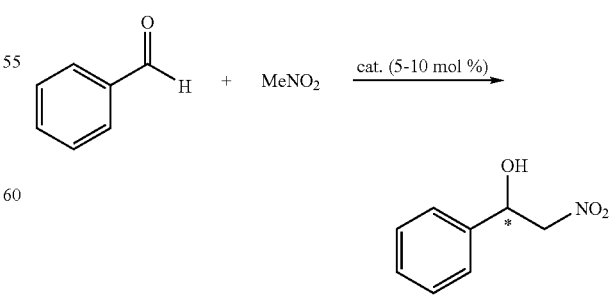

Under nitrogen atmosphere, the guanidine compound (C) (7.6 mg, 0.01 mmol) obtained in Example 3, THF (1.0 mL)

and benzaldehyde (20.3 μL, 0.20 mmol) were added, and the mixture was cooled to −40° C., and then nitromethane (108 μL, 2.0 mmol) was dropwise added thereto. After completion of the addition, the mixture was stirred for 23 hours, and the reaction was stopped using 1 mol/L hydrochloric acid-methanol solution. After further addition of 1 mol/L hydrochloric acid, the mixture was extracted with diethyl ether, and the organic layer was washed with water. After drying the extract over sodium sulfate, the solvent was evaporated, and the residue was purified by silica gel column chromatography (hexane/ethyl acetate=8/1) to obtain 31.7 mg (0.190 mmol, 95%, 46% ee) of a nitroaldol adduct. The product had an absolute configuration of (S)-form.

The optical purity was measured by liquid chromatography (Chiralcel OD-H, hexane/IPA=90/10, (R)-form=15.9 min, (S)-form=20.2 min).

$^1$H-NMR (CDCl$_3$) δ: 7.46-7.33 (5H, m), 5.48 (1H, ddd, J=3.2, 4.1, 9.2 Hz), 4.62 (1H, dd, J=9.2, 13.5 Hz), 4.52 (1H, dd, J=3.2, 13.5 Hz), 2.78 (1H, d, J=4.1 Hz)

Examples 13 to 28

Asymmetric Nitroaldol Reaction

According to the same manner as that of Example 12 except that the guanidine compound, the aldehyde and the solvent were variously changed in Example 12, and using the same reaction temperature, the reactions were performed. The results are shown in Table 1.

TABLE 1

| Example | Catalyst (mol %) | Aldehyde | Solvent | Time (h) | Yield (%) | Optical purity (%) |
|---|---|---|---|---|---|---|
| 13 | A (10) | A | THF | 19 | 63 | <1 |
| 14 | B (10) | A | Toluene | 20 | 59 | 4 (S) |
| 15 | B (10) | A | CH$_2$Cl$_2$ | 20 | 66 | 14 (S) |
| 16 | B (10) | A | THF | 20 | 90 | 19 (S) |
| 17 | C (10) | A | THF | 19 | 81 | 48 (S) |
| 18 | D (10) | A | THF | 21 | 81 | 2 (S) |
| 19 | E (5) | A | THF | 22 | 93 | 34 (S) |
| 20 | G (10) | A | THF | 22 | 84 | 17 (S) |
| 21 | C (5) | A | THF | 23 | 95 | 46 (S) |
| 22 | C (10) | A | DMF | 20 | 99 | 7 (S) |
| 23 | C (10) | A | CH$_3$CN | 21 | 87 | 13 (S) |
| 24 | C (10) | A | AcOEt | 24 | 74 | 34 (S) |
| 25* | C (10) | A | THF | 15 | 47 | 60 (S) |
| 26 | C (10) | B | THF | 23 | 40 | 47 |
| 27 | C (10) | C | THF | 5 | 28 | 40 |
| 28 | C (10) | D | THF | 5 | 50 | 38 |

*The reaction was performed at −78° C.
Aldehyde A: benzaldehyde
Aldehyde B: hydrocinnamaldehyde
Aldehyde C: p-tolualdehyde
Aldehyde D: o-tolualdehyde Examples 29 to 49

Asymmetric Nitroaldol Reaction (Henry Reaction)

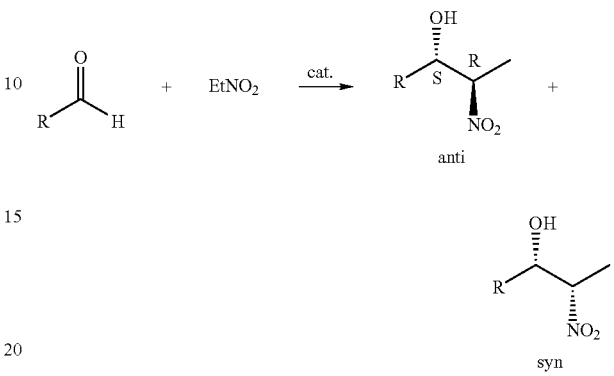

Under nitrogen atmosphere, each of various guanidine compounds (0.01 mmol) of the present invention as a catalyst, THF (1.0 mL) and aldehyde (0.20 mmol) were added, and the mixture was cooled and nitroethane (108 μL, 2.0 mmol) was dropwise added thereto. After completion of the dropwise addition, the mixture was stirred for 23 hours, and the reaction was stopped using 1 mol/L hydrochloric acid-methanol solution. After further addition of 1 mol/L of hydrochloric acid, the mixture was extracted with diethyl ether, and the organic layer was washed with water. After drying the extract over sodium sulfate, the solvent was evaporated, and the residue was purified by silica gel column chromatography (hexane/ethyl acetate=8/1) to obtain a nitroaldol adduct. Absolute configuration and optical purity were measured by liquid chromatography (Chiralcel AD-H, hexane/IPA=95/5, anti: (S,R)-form=14.8 min, (R,S)-form=17.3 min, syn: (f)-form=20.8 min, (b)-form=23.8 min).

anti form: $^1$H-NMR (CDCl$_3$) δ: 7.44-7.32 (5H, m), 5.41 (1H, dd, J=3.2, 3.5 Hz), 4.69 (1H, dq, J=3.5, 6.8 Hz), 2.69 (1H, d, J=3.2 Hz), 1.41 (3H, d, J=6.8 Hz)

syn form: $^1$H-NMR (CDCl$_3$) δ: 7.44-7.32 (5H, m), 5.03 (1H, dd, J=3.8, 8.9 Hz), 4.80 (1H, dq, J=8.9, 6.5 Hz), 2.56 (1H, d, J=3.8 Hz), 1.32 (3H, d, J=6.5 Hz)

The results are shown in the following Table.

TABLE 2

| Example | Catalyst | R | Solvent | Temperature (° C.) | Time (h) | Yield (%) | anti:syn | ee(%) anti, syn |
|---|---|---|---|---|---|---|---|---|
| 29 | A | Ph | THF | −40 | 13 | 62 | 78:23 | 5(S,R), 5(b) |
| 30 | C | Ph | THF | −40 | 12 | 95 | 79:21 | 57(S,R), 67(f) |
| 31 | C | Ph | THF | −40 | 2 | 50 | 79:21 | 57(S,R), 67(f) |
| 32 | E | Ph | THF | −40 | 12 | 89 | 87:13 | 30(S,R), 31(f) |

TABLE 2-continued

| Example | Catalyst | R | Solvent | Temperature (°C.) | Time (h) | Yield (%) | anti:syn | ee(%) anti, syn |
|---|---|---|---|---|---|---|---|---|
| 33 | F | Ph | THF | −40 | 13 | 99 | 79:11 | 28(S,R), 31(f) |
| 34 | H | Ph | THF | −40 | 13 | 95 | 80:20 | 2(R, S), 30(f) |
| 35 | C | Ph | Toluene | −40 | 13 | 33 | 76:24 | 35(S,R), 36(f) |
| 36 | C | Ph | CH$_2$Cl$_2$ | −40 | 13 | 32 | 72:28 | 24(S,R), 20(f) |
| 37 | C | Ph | TBME | −40 | 12 | 92 | 81:19 | 58(S,R), 59(f) |
| 38 | C | Ph | Et$_2$O | −40 | 12 | 99 | 76:24 | 53(S,R), 65(f) |
| 39 | C | Ph | n-Bu$_2$O | −40 | 12 | 94 | 79:21 | 57(S,R), 68(f) |
| 40 | C | Ph | CPME | −40 | 12 | 99 | 79:21 | 57(S,R), 70(f) |
| 41 | C | Ph | THF | −78 | 12 | 15 | 79:21 | 76(S,R), 88(f) |
| 42 | C | Ph | THF | −80 | 65 | 72 | 79:21 | 78(S,R), 87(f) |
| 43 | C | Ph | TBME | −80 | 70 | 49 | 87:13 | 77(S,R), 70(f) |
| 44 | C | o-tolyl | THF | −80 | 72 | 75 | 94:6 | 69(f), 74(f) |
| 45 | C | o-tolyl | THF | −80 | 72 | 56 | 76:24 | 81(f), 89(f) |
| 46 | C | o-bromo-phenyl | THF | −80 | 72 | 66 | 87:13 | 56(f), 10(b) |
| 47 | C | α-naphthyl | THF | −80 | 72 | 79 | 91:9 | 56(f), 47(f) |
| 48 | C | β-naphthyl | THF | −80 | 72 | 70 | 78:22 | 47(f), 50(f) |
| 49 | C | p-bromo-phenyl | THF | −80 | 72 | 81 | 80:20 | 58(f), 57(b) |

Examples 50 to 64

Asymmetric Epoxidation Reaction

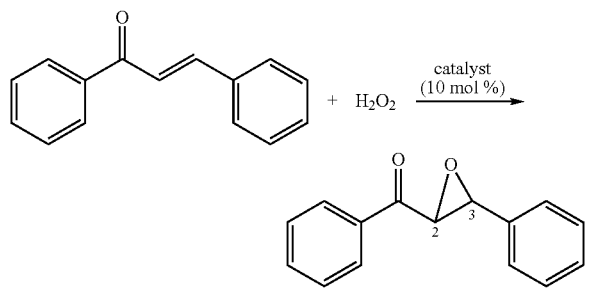

Each of various guanidine compounds (0.01 mmol) of the present invention as a catalyst, and chalcone (20.8 mg, 0.1 mmol) were weighed into a reaction vessel in which a stirrer had been placed, and the mixture was dissolved in toluene (1.0 mL). Aqueous hydrogen peroxide (30 wt %, 21 µL, 0.2 mmol) was added to the solution at room temperature, and the mixture is stirred, and then an aqueous sodium sulfite solution was added to stop the reaction. After extraction with ethyl acetate, the resulting organic layer was dried over sodium sulfate, and the solvent was evaporated. The residue was purified by column chromatography to obtain an epoxy compound. The optical purity was measured by liquid chromatography (Chiralcel AD-H, hexane/EtOH=90/10, 1.0 mL/min, (2R,3S)=27.0 min, (2S,3R)=35.4 min).

$^1$H-NMR (CDCl$_3$) δ: 8.02 (2H, d, J=7.5 Hz), 7.63 (1H, t, J=7.5 Hz), 7.49 (2H, t, J=7.5 Hz), 7.45-7.35 (5H, m), 4.30 (1H, d, J=1.6 Hz), 4.08 (1H, d, J=1.6 Hz)

$^{13}$C-NMR(CDCl$_3$) δ: 193.0, 135.4, 133.9, 129.0, 128.8, 128.7, 128.2, 125.7, 60.9, 59.3

The results are shown in the following Table 3.

TABLE 3

| Example | Catalyst | Solvent | Time | Yield (%) | Optical purity ee(%) |
|---|---|---|---|---|---|
| 50 | C | CH$_2$Cl$_2$ | 9 h | 52 | 18 (2R,3S) |
| 51 | C | Toluene | 9 h | 66 | 32 (2R,3S) |
| 52 | C | Et$_2$O | 9 h | 48 | 9 (2R,3S) |
| 53 | E | Toluene | 24 h | 41 | 4 (2S,3R) |
| 54 | F | CH$_2$Cl$_2$ | 9 h | 76 | 7 (2R,3S) |
| 55 | F | Toluene | 9 h | 55 | 11 (2S,3R) |
| 56 | F | Et$_2$O | 9 h | 93 | 4 (2R,3S) |
| 57 | G | CH$_2$Cl$_2$ | 9 h | 43 | 4 (2R,3S) |
| 58 | G | Toluene | 9 h | 62 | 8 (2S,3R) |
| 59 | G | Et$_2$O | 9 h | 50 | 5 (2R,3S) |
| 60 | H | CH$_2$Cl$_2$ | 3 h | 85 | 7 (2R,3S) |
| 61 | H | Et$_2$O | 10 h | 76 | 10 (2R,3S) |
| 62 | I | Toluene | 9 h | 56 | 16 (2S,3R) |
| 63 | J | Toluene | 9 h | 48 | 53 (2S,3R) |
| 64 | K | Toluene | 8 h | 74 | 44 (2S,3R) |

Example 65

Asymmetric Michael Addition Reaction

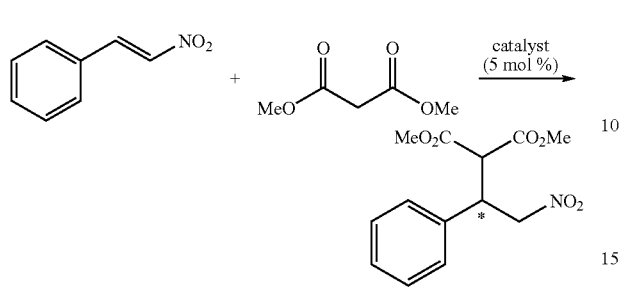

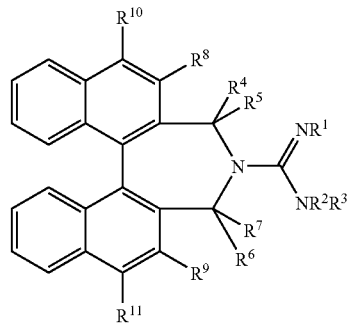

β-nitrostyrene (14.9 mg, 0.10 mmol) was added to a reaction vessel in which a stirrer had been placed, and the material was dissolved in THF (1.0 mL). After cooled to 0° C., dimethyl malonate (58 μL, 0.5 mmol) was added thereto. A guanidine compound C (3.8 mg, 0.005 mmol) as a catalyst was weighed into the resulting solution in a nitrogen atmosphere. After stirring for 2 hours, the reaction was stopped using 1 mol/L of a solution of hydrochloric acid in methanol, and 1 mol/L hydrochloric acid was added thereto. The mixture was extracted with diethyl ether, and the organic layer was washed with water. After drying using sodium sulfate, the solvent was evaporated, and the residue was purified by silica gel chromatography (hexane/ethyl acetate) to quantitatively obtain a Michael adduct as a (R)-form (28.1 mg, 0.10 mmol, 21% ee).

The optical purity was measured by liquid chromatography (Chiralcel AD-H, hexane/IPA=90/10, 1.5 mL/min, (S)=14.6 min, (R)=28.7 min).

INDUSTRIAL APPLICABILITY

The guanidine compound of the present invention is useful as a catalyst for an asymmetric addition reaction such as an asymmetric aldol-type reaction, an asymmetric Michael addition reaction and an asymmetric epoxidation reaction and the like.

The invention claimed is:

1. A guanidine compound having a biaryl skeleton represented by the following formula (Z):

wherein $R^1$, $R^2$ and $R^3$ each independently represent a hydrogen atom, a hydrocarbon group optionally having substituent(s), or a heterocyclic group optionally having substituent(s);

$R^4$, $R^5$, $R^6$, $R^7$, $R^8$, $R^9$, $R^{10}$ and $R^{11}$ each independently represent a hydrogen atom, a hydrocarbon group optionally having substituent(s), a heterocyclic group optionally having substituent(s), a hydroxy group, an alkoxy group optionally having substituent(s), an aryloxy group optionally having substituent(s), an acyl group, an alkoxycarbonyl group optionally having substituent(s), an aryloxycarbonyl group optionally having substituent(s), a carbamoyl group optionally having substituent(s), an alkylthiocarbonyl group optionally having substituent(s), an arylthiocarbonyl group optionally having substituent(s), a carboxyl group, an alkylthio group optionally having substituent(s), an arylthio group optionally having substituent(s), an amino group or a substituted amino group, a substituted silyl group or a halogen atom.

2. The guanidine compound according to claim 1, which is optically active.

3. The optically active guanidine compound according to claim 2, which is an optically active form due to axial chirality.

* * * * *